(12) United States Patent
Yang et al.

(10) Patent No.: US 10,174,067 B2
(45) Date of Patent: Jan. 8, 2019

(54) TYPE OF CYTIDINE DERIVATIVE AND APPLICATION THEREOF

(71) Applicants: CHANGZHOU FANGYUAN PHARMACEUTICAL CO., LTD, Changzhou (CN); INNER MONGOLIA PUYIN PHARMACEUTICAL CO., LTD., Chifeng (CN)

(72) Inventors: Daria Yang, Changzhou (CN); Haidong Wang, Changzhou (CN); Xin Liu, Changzhou (CN); Huijuan Wang, Changzhou (CN)

(73) Assignees: CHANGZHOU FANGYUAN PHARMACEUTICAL CO., LTD, Changzhou (CN); INNER MONGOLIA PUYIN PHARMACEUTICAL CO., LTD, Chifeng (CN)

( * ) Notice: Subject to any disclaimer, the term of this patent is extended or adjusted under 35 U.S.C. 154(b) by 0 days.

(21) Appl. No.: 15/527,313

(22) PCT Filed: Jun. 9, 2015

(86) PCT No.: PCT/CN2015/081047
§ 371 (c)(1),
(2) Date: May 16, 2017

(87) PCT Pub. No.: WO2016/078397
PCT Pub. Date: May 26, 2016

(65) Prior Publication Data
US 2017/0355726 A1 Dec. 14, 2017

(30) Foreign Application Priority Data

Nov. 17, 2014 (CN) .......................... 2014 1 0653980
Apr. 9, 2015 (CN) .......................... 2015 1 0167477

(51) Int. Cl.
*C07H 19/06* (2006.01)
*A61K 9/00* (2006.01)
*A61K 31/7068* (2006.01)

(52) U.S. Cl.
CPC .......... *C07H 19/06* (2013.01); *A61K 9/0019* (2013.01); *A61K 31/7068* (2013.01)

(58) Field of Classification Search
None
See application file for complete search history.

(56) References Cited

U.S. PATENT DOCUMENTS

2014/0134160 A1* 5/2014 Wu ........................ C07H 19/06
424/133.1

FOREIGN PATENT DOCUMENTS

| WO | 9115498 A2 | 10/1991 |
| WO | 2004041203 A2 | 5/2004 |
| WO | 2006111058 A1 | 10/2006 |

OTHER PUBLICATIONS

The World Intellectual Property Organization (WIPO) International Search Report for PCT/CN2015/081047, 5 pages, dated May 26, 2016.
The European Patent Office (EPO) The Extended European Search Report for 15860978.4 dated Oct. 10, 2017 9 Pages.
Guo Z-W et al: "Selective Protection of 2′, 2′-Difluorodeoxycytidine (Gemcitabine)", The Journal of Organic Chemistry, American Chemical Society Etc. I, vol. 64, No. 22, Oct. 29, 1999 (Oct. 29, 1999), pp. 8319-8322, XP003003100, ISSN: 0022-3263, DOI: 10.1021/JO9911140.
Jason T. Weiss et al: "Development and Bioorthogonal Activation of Palladium-Labile Prodrugs of Gemcitabine", Journal of Medicinal Chemistry, vol. 57, No. 12, Jun. 26, 2014 (Jun. 26, 2014), pp. 5395-5404, XP055408793, ISSN: 0022-2623, DOI: 10.1021/jm500531z.
Kim K-H et al: "Synthesis and biological activity of the new 5-fluorocytosine derivatives, 5′-deoxy-N-alkoxycarbonyl-5-fluorocytosine-5′-carboxylic acid", Bioogranic & Medicinal Chemistry Letters, Pergamon, Amsterdam, NL, vol. 12, No. 3, Jan. 1, 2002 (Jan. 1, 2002), pp. 483-486, XP001154721, ISSN: 0960-894X, DOI: 10.1016/S0960-894X(01)00782-X.

* cited by examiner

*Primary Examiner* — Traviss C McIntosh, III
(74) *Attorney, Agent, or Firm* — Anova Law Group, PLLC

(57) ABSTRACT

The present disclosure provides a new cytidine derivative having the general formula (I), and applications thereof:

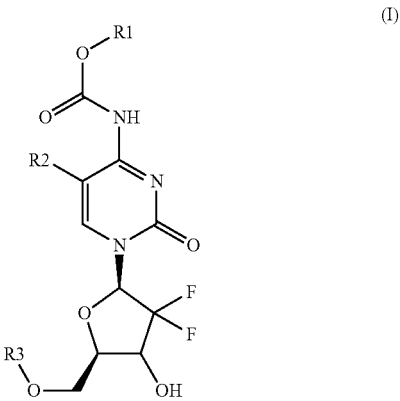

As demonstrated by experiments on the growth inhibition effect of the new cytidine derivative of the present invention on HCT-116 colon cancer xenografts in tumor-bearing nude mice, the compound of the present invention has high anti-tumor activity, data of impacts on weight of nude mice bearing human colon cancer HCT-116 and data of mortality rate showed that the toxicity of the compound is comparatively low.

9 Claims, No Drawings

TYPE OF CYTIDINE DERIVATIVE AND APPLICATION THEREOF

TECHNICAL FIELD

The present invention relates to a new type of cytidine derivative and applications of derivatives in preparation of anti-tumor drugs.

BACKGROUND TECHNOLOGIES

Malignant tumor is one of the common diseases that threaten human health, and ranks first among all diseases in terms of mortality rate. Regarding anti-tumor drugs available in current clinical application, their toxicity is a prominent problem in tumor chemotherapy. Improving the effectiveness of tumor treatment and simultaneously reducing drug toxicity are the key study subjects on current cancer drugs.

Cytidine derivatives having anti-tumor effects includes cytarabine and gemcitabine. Cytarabine is turned into active triphosphate cytarabine in the body to achieve anti-cancer effect. Triphosphate cytarabine prevents DNA synthesis and inhibits cell growth by inhibiting NDA polymerase and inserting a small amount of DNA, which is mainly used for the treatment of acute myeloblastic leukemia. However, cytarabine has comparatively great toxic side-effects, which may cause bone marrow suppression, white blood cell reduction and thrombocytopenia to the hematopoietic system. Aplastic anemia or megaloblastic anemia may occur in severe cases. Hyperuricemia may occur for the patient with leukemia or lymphoma inearly treatment, and uric acid nephropathy may occur in severe cases.

Gemcitabine is a derivative of deoxycytidine, and is similar to cytarabine in structure and metabolism. Gemcitabine is, through nucleoside monophosphate kinase in the cell, catalyzed into activated Dipridecyl diphosphate (dFdCDP) and Tripolytic acid triphosphate (dFdCTP), and dFdCTP impedes DNA synthesis through inhibiting DNA polymerase. The DNA chain discontinues to extend clue to the incorporation to DNA, thereby inhibiting the growth of tumor cells.

Gemcitabine is applicable for pancreatic cancer (primary and secondary treatments), non-small cell lung cancer, breast cancer, ovarian cancer, and head and neck squamous cell carcinoma. However, the toxicity of gemcitabine is also relatively great. Its adverse reactions are bone marrow suppression, such as leucopenia, thrombocytopenia and anemia; gastrointestinal reactions such as mild nausea, vomiting and abnormal liver function; fever, flu-like symptoms, fatigue, mucositis and so on.

After the above-mentioned cytidine derivatives enter the human body, the tumor cells will produce multi-drug resistance gene. Besides, the amino on the ring are easily acetylated, causing loss of compound anticancer activity and other resistance factors. The above-mentioned cytidine derivatives have great toxic side-effects, and tend to produce drug resistance.

In order to reduce the toxicity of cytarabine and gemcitabine, and improve or maintain anti-tumor efficacy, researchers modify the chemical structure of cytidine derivatives.

For example, Synthesis and Biological Activity of a Gemcitabine Phosphoramidate Prodrug (J. Med. Chem 2007, 50, 3743-3746; Weidong Wu) reported a kind of gemcitabine phosphate prodrug.

U.S. Pat. No. 7,265,096 B2 (application Ser. No. 10/701,965) disclosed gemcitabine prodrugs, pharmaceutical compositions and uses thereof. This article substituted the amino of gemcitabine, hydrogen atom of hydroxyl and hydrogen atom of hydroxymethyl on ribofuranose. The hydrogen atom of hydroxymethyl on the ribofuranose was substituted by H, acyl, substituent acyl, acyloxy-carbonyl, substituent acyloxy-carbonyl, oxy-carbonyl and substituent oxy-carbonyl; the hydrogen atom of hydroxyl on the ribofuranose was substituted by H, acyl, substituent acyl, acyloxy-carbonyl, substituent acyloxy-carbonyl, oxy-carbonyl and substituent oxy-carbonyl; the amino was substituted by $-N=C(R^{10})(R^{11})$ or $-NHR^{12}$, wherein, $R^{12}$ was $C_5$-$C_9$ acyl or $C_5$-$C_9$ substituent acyl. The compound prepared by this patent is a prodrug that only exhibits anti-tumor activity after transformation in the body. In addition, clinical studies discover that gemcitabine prodrug has high toxicity and low anti-tumor activity, which is not yet developed as a medicine.

SUMMARY OF THE INVENTION

The technical problem solved by the present invention is providing a new type of cytidine derivative and application of such derivatives in preparation of anti-tumor drugs.

The technical solution for achieving the objective of the present invention includes: a new type of cytidine derivative having the following general formula (I):

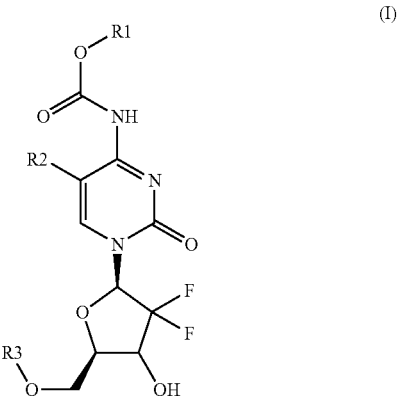

Wherein, R1 is $C_1$-$C_{10}$ alkyl, $C_1$-$C_{10}$ substituent alky, $-(CH_2)n$-Ph, or substituent $-(CH_2)n$-Ph; wherein in said $-(CH_2)n$-Ph, n=0, 1, 2, 3 to 10, Ph is phenyl; a carbon chain of said substituent alkyl is independently substituted by one or two or three halogen, cyano group, nitro group, amino group, hydroxy group or carboxyl group; in said substituent $-(CH_2)n$-Ph, n=0, 1, 2, 3 to 10, and a carbon chain or a phenyl ring of which is independently substituted by one or two or three halogen, cyano group, nitro group, amino group, hydroxyl group or carboxyl group.

R2 is H, halogen, or

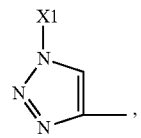

wherein X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —($C_2$)n-Ph, or substituent —($CH_2$)n-Ph; wherein a carbon chain of said substituent alkyl is substituted independently by one or two or three halogen, cyano group, nitro group, amino group, hydroxyl group or carboxyl group; a carbon chain of said substituent alkoxy is substituted independently by one or two or three halogen, cyano group, nitro group, amino group, hydroxyl group or carboxyl group; in said ($CH_2$) n-Ph, n=0, 1, 2, 3 to 10; in said substituent ($CH_2$) n-Ph, n=0, 1, 2, 3 to 10, and a carbon chain or a phenyl ring of which is substituted by one or two or three H, halogen, cyano group, nitro group, amino group, hydroxyl group or carboxyl group.

R3 is H or

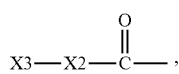

wherein X3 is phenyl ring, heterocyclic ring, fused heterocyclic ring, substituent phenyl that is substituted independently by one or two or three halogen, cyano group, nitro group, amino group, hydroxyl group or carboxyl group, substituent heterocyclic ring that is substituted independently by one or two or three halogen, cyano group, nitro group, amino group, hydroxyl group or carboxyl group, or substituent fused heterocyclic ring that is substituted independently by one or two or three halogen, cyano group, nitro group, amino group, hydroxyl group or carboxyl group; wherein said heterocyclic ring is imidazole, pyridine, furan, thiophene, thiazole, pyrimidine, piperazine or piperidine; said fused heterocyclic ring is quinoline or indole; and X2 is —($CH_2$)n-, wherein n=1, 2, 3, or X2 is —O—($CH_2$)n-, wherein n=0, 1, 2, 3.

Optionally, R2 is H.

Preferably, R2 is not H; and R3 is not H.

When R2 is not H, R2 is halogen or

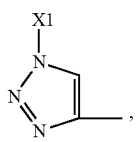

X1 is —($CH_2$)n-Ph or substituent —($CH_2$)n-Ph.

Preferably, R1 is $C_1$-$C_4$ alkyl, $C_1$-$C_4$ substituent alkyl, benzyl, or substituent benzyl; X3 of R3 is substituent imidazole substituted independently by one or two or three halogen, cyano group, nitro group, amino group, hydroxyl group or carboxyl group, substituent pyridine substituted independently by one or two or three halogen, cyano group, nitro group, amino group, hydroxyl group or carboxyl group, or substituent phenyl ring substituted independently by one or two or three halogen, cyano group, nitro group, amino group, hydroxyl group or carboxyl group.

The applications of the above compounds or their salts in preparation of anti-tumor drugs.

The tumor refers to blood tumor or malignant solid tumor.

The salt refers to hydrochloride, phosphate, sulfate, carbonate, nitrate, citrate, tartrate, maleate, succinate, sulfonate, p-toluenesulfonate, mesylate, benzoate or fumarate.

A pharmaceutical composition includes; a cytidine derivative as shown by formula (I) or a pharmaceutically acceptable salt thereof as an active ingredient, and one or more pharmaceutical carriers or excipients.

The dosage form of the above-mentioned composition is injection or oral perpetration, wherein the injection refers to solution, type injection, suspension type injection, emulsion type injection, or sterile powder for injection; the oral perpetration refers to tablet, powder, granule, capsule, pellet, solution, suspension, emulsion, syrup or elixir.

The present invention has advantageous effects; as demonstrated by experiments on growth inhibition effect of the compound disclosed in the present invention on HCT-116 colon cancer xenografts in tumor-bearing nude mice, the compound disclosed in the present invention has high anti-tumor activity and little impact on the weight of nude mice bearing human colon cancer HCT-116, which demonstrates that the toxicity of the compound is relatively low.

DETAILED DESCRIPTION

The new cytidine derivative in the present invention has the following structural formula (I);

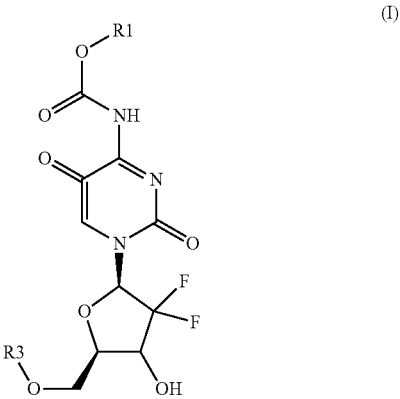

Wherein, R1 is $C_1$-$C_{10}$ alkyl, $C_1$-$C_{10}$ substituent alkyl, —($CH_2$)n-Ph, or substituent —($CH_2$)n-Ph; in said —($CH_2$) n-Ph, n=0, 1, 2, 3 to 10, Ph is phenyl; carbon chain of said substituent alkyl is substituted independently by one or two or three halogen, cyano, nitro, amino, hydroxyl or carboxyl; in said substituent —($CH_2$)n-Ph, n=0, 1, 2, 3 to 10, and the carbon chain or the phenyl ring thereof is substituted independently by one or two or three halogen, cyano, nitro, amino, hydroxyl or carboxyl.

R2 is H, halogen, or

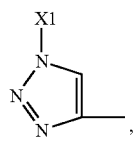

wherein X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —($CH_2$)n-Ph, or substituent —($CH_2$)n-Ph; the carbon chain of said substituent alkyl is substituted independently by one or two or three halogen, cyano, nitro, amino, hydroxyl or carboxyl; the carbon chain of said substituent alkoxy is substituted independently by one or two or three halogen, cyano, nitro, amino, hydroxyl or carboxyl; in said ($CH_2$) n-Ph, n=0, 1, 2, 3 to 10; in said substituent ($CH_2$) n-Ph, n=0, 1, 2, 3 to 10, and the carbon chain or phenyl ring of which is substituted by one or two or three H, halogen, cyano, nitro, amino, hydroxyl or carboxyl.

R3 is H or

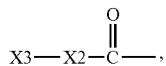

wherein X3 is phenyl ring, heterocyclic ring or fused heterocyclic ring, substituent phenyl that is substituted independently by one or two or three halogen, cyano, nitro, amino, hydroxyl or carboxyl, substituent heterocyclic ring that is substituted independently by one or two or three halogen, cyano, nitro, amino, hydroxyl or carboxyl, or substituent fused heterocyclic ring that is substituted independently by one or two or three halogen, cyano, nitro, amino, hydroxyl or carboxyl; said heterocyclic ring is imidazole, pyridine, furan, thiophene, thiazole, pyrimidine, piperazine or piperidine; said fused heterocyclic ring is quinoline or indole; X2 is —(CH$_2$)n-, wherein n=1, 2, 3, or X2 is —O—(CH$_2$)n-, wherein n=0, 1, 2, 3.

Regarding cytidine derivative of the present invention, Table 1 lists the following compounds. However, the cytidine derivatives of the present invention are not limited to these compounds.

TABLE 1

| Compound No. | Code | Substituent Group |
|---|---|---|
| 1 | G2 | R1 is n-butyl, R2 is H, and R3 is H |
| 2 | G3 | R1 is tert-butyl, R2 is H, and R3 is H |
| 3 | G4 | R1 is benzyl, R2 is H, and R3 is H |
| 4 | G5 | R1 is 4-nitrobenzyl, R2 is H, and R3 is H |
| 5 |  | R1 is 2,4-dinitrobenzyl, R2 is H, and R3 is H |
| 6 |  | R1 is 2,4,6-trinitrobenzyl, R2 is H, and R3 is H |
| 7 |  | R1 is 4-aminobenzyl, R2 is H, and R3 is H |
| 8 | G6 | R1 is n-butyl, R2 is Br, and R3 is H |
| 9 | G7 | R1 is benzyl, R2 is Br, and R3 is H |
| 10 |  | R1 is 4-cyanobenzyl, R2 is Br, and R3 is H |
| 11 |  | R1 is 4-carboxybenzyl, R2 is Br, and R3 is H |
| 12 | G8 | R1 is n-butyl, R2 is H, and R3 is (2-hydroxy-3-methyl-4,6-dinitrophenyl) |
| 13 |  | R1 is n-octyl, R2 is H, and R3 is (2-hydroxy-3-methyl-4,6-dinitrophenyl) |
| 14 |  | R1 is n-hexyl, R2 is H, and R3 is (2-hydroxy-3-methyl-4,6-dinitrophenyl) |
| 15 | G9 | R1 is tert-butyl, R2 is H, and R3 is (1-ethyl-4-nitroimidazolyl) |
| 16 | G10 | R1 is benzyl, R2 is Br, and R3 is (3,5,6-trichloropyridin-2-yloxy)acetonyl |

TABLE 1-continued
| Compound No. | Code | Substituent Group |
|---|---|---|
| 17 | | R1 is benzyl, R2 is Br, and R3 is 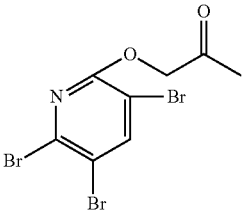 |
| 18 | G11 | R1 is n-butyl, R2 is I, and R3 is 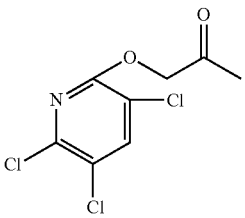 |
| 19 | G12 | R1 is n-butyl, R2 is I, and R3 is 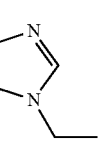 |
| 20 | G13 | R1 is 4-nitrobenzyl, R2 is , and R3 is  |
| 21 | | R1 is 4-nitrobenzyl, R2 is substituent 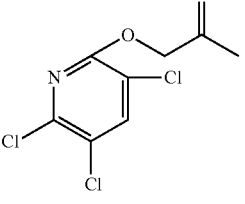, position 4 of the benzene ring is substituted by nitro, and R3 is  |

TABLE 1-continued

| Compound No. | Code | Substituent Group |
|---|---|---|
| 22 | G14 | R1 is benzyl, R2 is 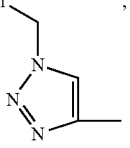, and R3 is 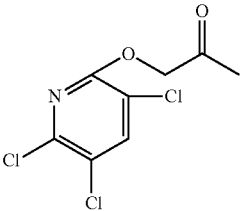 |
| 23 | G15 | R1 is n-butyl, R2 is 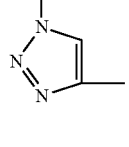, and R3 is 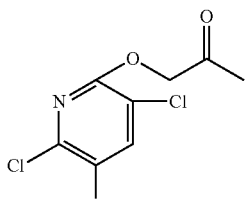 |
| 24 |  | R1 is n-butyl, R2 is substituent 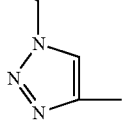, position 4 of the benzene ring is substituted by Cl, and R3 is 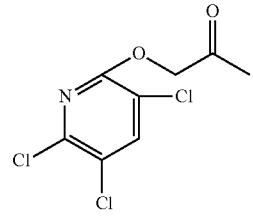 |
| 25 | G16 | R1 is n-butyl, R2 is Br, and R3 is 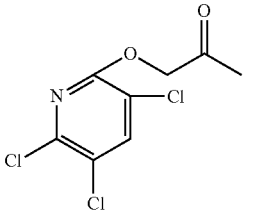 |
| 26 | G17 | R1 is 4-nitrobenzyl, R2 is Br, and R3 is the same as G16. |

When preparing the compounds in the table above, the solid reagents employed in the synthesis process are used directly without further treatment, the liquid reagents are used after redistilled and dried.

Example 1

The cytidine derivative of the present example is 4-N-(n-butoxycarbonyl)-2'-deoxy-2',2'-difluorocytidine (structural formula: 4, code: G2), which can be prepared through three steps of reaction. The reaction formula is shown below (in the reaction formula, HMDS is hexamethyldisilazane, rt is room temperature, and TEA is triethylamine, the abbreviations are the same in the following).

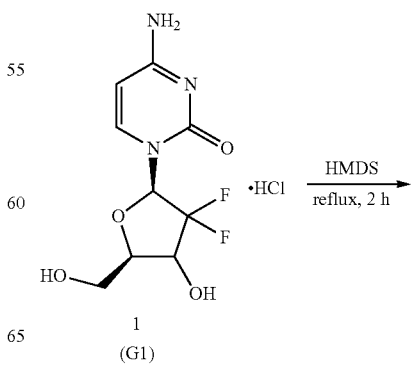

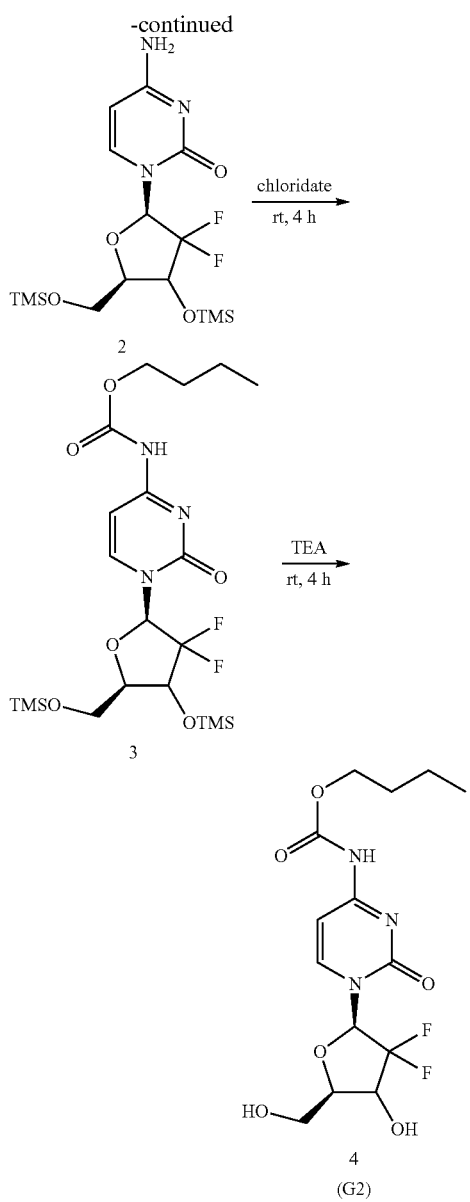

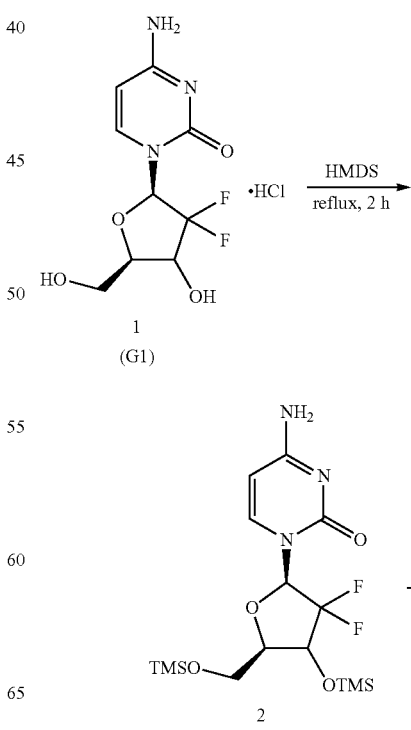

300 mg (1 mmol) of 2'deoxy-2',2'-difluorocytidine hydrochloride (structural formula: 1, code: G1), 5 mL (0.023 mmol) of Bis(trimethylsilyl)amine HMDS and 5 mg of ammonium sulfate in catalytic amount were dissolved in 5 mL of 1,4-dioxane, and heated under reflux for 2 h. The chemical structural formula of the reaction product was 2. After the reaction under reflux was completed, the reaction liquid was concentrated, added with toluene, and concentrated to dryness twice. The resulting product after concentrating was dissolved in 10 mL of dichloromethane.

0.24 mL (3 mmol) of N-methylimidazole and 0.32 mL (3 mmol) of n-butyl chloroformate were added into the above dichloromethane solution, for a reaction with stirring at room temperature for 4 h. The chemical structural formula of the reaction product was 3, and the reaction liquid was concentrated to provide a viscous oily product.

The viscous oily product was dissolved in a mixed solution of 3 mL of triethylamine and 20 mL of methanol, and stirred at room temperature for 4 h. The solvent was removed by distillation under reduced pressure. Silica gel chromatography was performed to purify the crude product, and 230 mg of G2 was obtained alter the elution by dichloromethane/methanol (20:1). The three-step reaction yield was 55.5%.

NMR characterization of G2:

$^1$H-NMR (MeOD-$d_4$, 400 MHz) δ: 8.30 (d, 1H, J=7.68 Hz, H6), 7.34 (d, 1H, J=7.68 Hz, H5), 6.28 (t, 1H, J=7.08 Hz, H1') 4.33 (m, 1H, H5a'), 4.0 (m, 2H, O—CH$_2$—C$_2$—), 3.81 (m, 1H, H5b'), 3.79 (m, 1H, H4'), 1.68 (m, 2H, O—CH$_2$—CH$_2$—), 1.45 (m, 2H, O—CH$_2$—CH$_2$—CH$_2$), 0.98 (t, 3H, J=7.4 Hz, —CH$_2$—CH$_3$).

$^{13}$C-NMR (MeOD-$d_4$, 100 MHz) δ: 164.28, 156.27, 153.50, 144.39, 128.33, 122.72, 95.81, 84.90, 81.71, 74.87, 68.88, 63.69, 59.15, 30.66, 32.40, 18.81, 11.23, 8.06.

The above preparation method can be adapted by changing the reaction raw materials. Other than n-butyl, R1 can be other groups, such as $C_1$-$C_{10}$ alkyl, $C_1$-$C_{10}$ substituent alkyl, —(CH$_2$)n-Ph, n=0, 1, 2, 3 to 10, or substituent —(CH$_2$)n-Ph, n=0, 1, 2, 3 to 10, Ph is phenyl; where the carbon chain in the substituent alkyl is substituted independently by one or two or three halogen, cyano, nitro, amino, hydroxyl or carboxyl; the carbon chain or the phenyl ring in said substituent —(CH$_2$)n-Ph is substituted independently by one or two or three halogen, cyano, nitro, amino, hydroxyl or carboxyl.

Example 2

The cytidine derivative of the present example is 4N-(t-butyloxycarbonyl)-2'deoxy-2',2'-difluorocytidine (structural formula: 6, code: G3), which can be prepared through three steps of reaction. The reaction formula is as below.

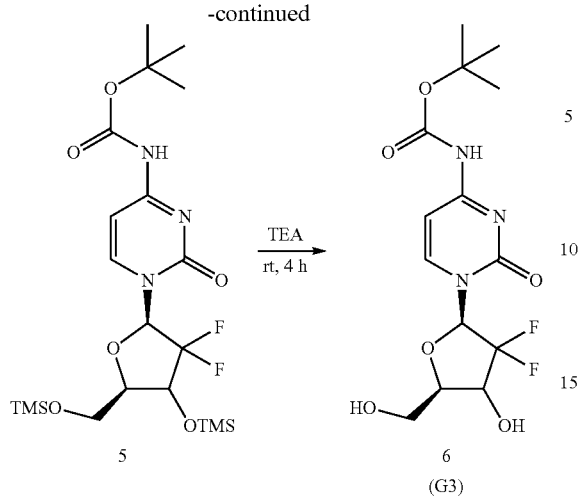

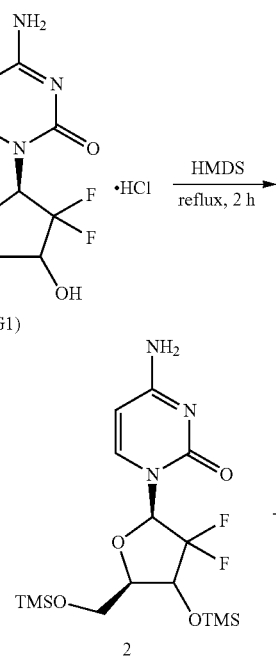

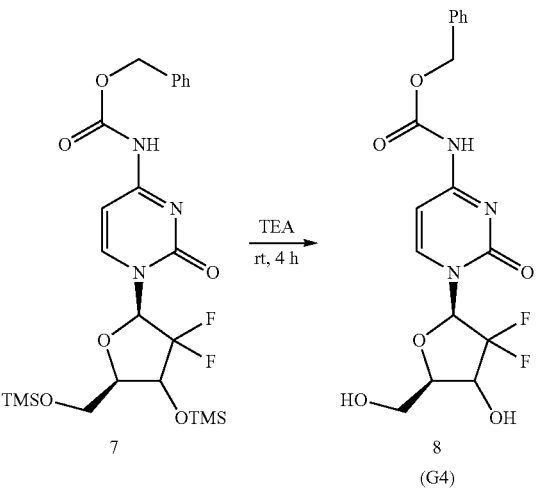

300 mg (1 mmol) of 2'-deoxy-2',2'difluorocytidine hydrochloride, 5 mL (0.023 mmol) of HMDS and 5 mg of ammonium sulfate in catalytic amount were dissolved in 5 mL of 1,4-dioxane, and heated under reflux, for 2 h. After the reaction under reflux was completed, the reaction liquid was concentrated, added with toluene, and concentrated to dryness twice. The resulting product after concentrating was dissolved in 10 mL of dichloromethane.

0.24 mL (3 mmol) of N-methylimidazole and 416 mg (3 mmol) of di-tert-butyl dicarbonate were added into the above dichloromethane solution, stirring to react at room temperature for 4 h. The chemical structural formula of the reaction product was 5, and the reaction liquid was concentrated to provide a viscous oily product.

The viscous oily product was dissolved in a mixed solution of 3 mL triethylamine and 20 mL methanol, and stirred at room temperature overnight. Then, the solvent was removed by distillation under reduced pressure. Silica gel chromatography was performed to purify the crude product, and 199 mg of G3 was obtained after the elution by dichloromethane/methanol (20:1). The three-step reaction yield was 54%.

NMR characterization of G3:

$^1$H-NMR (MeOD-d$_4$, 400 MHz) δ: 8.27 (d, 1H, J=7.68 Hz, H6), 7.32 (d, 1H, J=7.68 Hz, H5), 6.28 (t, 1H, J=7.08 Hz, H1') 4.25 (m, 1H, H5a'), 3.93 (m, 2H, H5b', H4'), 3.78 (m, 1H, H3'), 1.52 (s, 9H, t-Bu).

$^{13}$C-NMR (MeOD-d$_4$, 100 MHz) δ: 164.36, 152.17, 144.24, 125.29, 122.71, 120.13, 109.98, 95.78, 82.17, 81.60, 70.45, 69.30, 68.90, 65.57, 55.90, 27.12, 23.57.

Example 3

The cytidine derivative of the present example is 4-N-(carboxybenzyl)-2'-deoxy-2',2'-difluorocytidine (structural formula; 8, code: G4), which can be prepared through three steps of reaction. The reaction formula is as below.

300 mg (1 mmol) of 2'-deoxy-2',2'-difluorocytidine hydrochloride, 5 mL (0.023 mmol) of HMDS and 5 mg of ammonium sulfate in catalytic amount were dissolved in 5 mL of 1,4-dioxane, and heated under reflux for 2 h. After the reaction under reflux was completed, the reaction liquid was concentrated, added with toluene, and concentrated to dryness twice. The resulting product after concentrating was dissolved in 10 mL of dichloromethane.

0.24 mL (3 mmol) of N-methylimidazole and 340 mg (3 mmol) of carbobenzoxy chloride were added into the above dichloromethane solution, for a reaction with stirring at room temperature for 4 h. The chemical structural formula of the reaction product was 7, and the reaction liquid was concentrated to provide a viscous oily product.

The viscous oily product was dissolved in a mixed solution of 3 mL triethylamine and 20 mL methanol, and stirred at room temperature overnight. Then, the solvent was removed by distillation under reduced pressure. Silica gel chromatography was performed to purify the crude product and 162 mg of G4 was obtained after the elution by dichloromethane/methanol (20:1). The three-step reaction yield was 41%.

NMR characterization of G4:

$^1$H-NMR (MeOD-d$_4$, 400 MHz) δ: 8.31 (d, 1H, J=7.64 Hz, H6), 7.39 (m, 5H, J=7.68 Hz, Ph), 6.25 (t, 1H, J=7.12 Hz, H1'), 5.21 (s, 2H, CH$_2$-Ph), 4.31 (m, 1H, H5a'), 3.82 (m, 2H, H5b, H4'), 3.79 (m, 1H, H3').

$^{13}$C-NMR (MeOD-d$_4$, 100 MHz) δ: 164.22, 156.22, 153.27, 144.48, 135.87, 128.42, 128.10, 125.31, 122.74, 120.16, 95.89, 85.35, 84.91, 81.7, 81.66, 68.87, 67.54, 58.31.

Example 4

The cytidine derivative of the present example is 4-N-(4-nitrocarboxybenzyl)-2'-deoxy-2',2'-difluorocytidine (structural formula: 10, code: G5), which can be prepared through three steps of reaction. The reaction formula is as below.

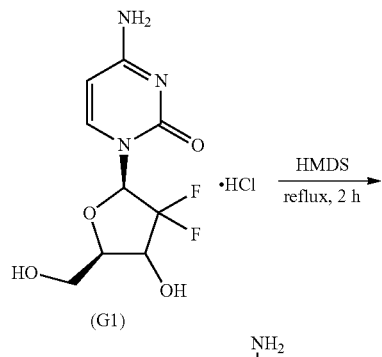

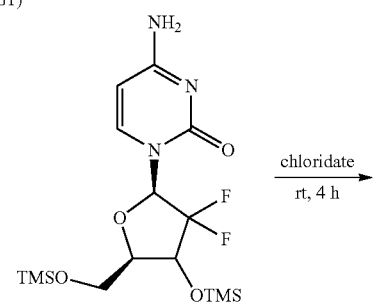

300 mg (1 mmol) of 2'-deoxy-2',2'-difluorocytidine hydrochloride, 5 mL (0.023 mmol) of HMDS and 5 mg of ammonium sulfate in catalytic amount were dissolved in 5 mL of 1,4-dioxane, and heated under reflux for 2 h. After the reaction under reflux was completed, the reaction liquid was concentrated, added with toluene, and concentrated to dryness twice. The resulting product after concentrating was dissolved in 10 mL of dichloromethane.

0.24 mL (3 mmol) of N-methylimidazole and 430 mg (3 mmol) of 4-nitrobenzyl chloroformate were added into the above dichloromethane solution, for a reaction with stirring at room temperature for 4 h. The chemical structural formula of the reaction product was 9, and the reaction liquid, was concentrated to provide a viscous oily product.

The viscous oily product was dissolved in a mixed solution of 3 mL triethylamine and 20 mL methanol, and stirred room temperature overnight. Then, the solvent was removed by distillation under reduced pressure. Silica gel chromatography was performed to purify the crude product, and 160 rag of G5 was obtained after the elution by dichfluoromethane/methanol (20:1). The three-step reaction yield was 36%.

NMR characterization of G5:

$^1$H-NMR (DMSO-d$_6$, 400 MHz) δ: 11.11 (s, 1H), 8.25 (m, 3H, Ph), 7.68 (d, 2H, J=8.64 Hz, Ph), 7.08 (d, 1H, J=7.44 Hz, H6), 6.29 (d, 1H, J=7.44 Hz, H5) 6.17 (t, 1H, J=7.4 Hz, H1'), 5.33 (s, 2H, CH$_2$-Ph), 5.29 (t, 1H, J=5.44 Hz), 4.19 (m, 1H, H5a'), 3.66 (m, 1H, H5b'), 3.61 (m, 1H, H4'), 3.29 (m, 1H, H3').

$^{13}$C-NMR (DMSO-d$_6$, 100 MHz) δ: 163.93, 153.47, 147.86, 144.38, 128.97, 126.72, 126.19, 124.26, 123.62, 95.57, 84.82, 83.99, 81.77, 71.91, 69.13, 68.42, 66.06, 62.34, 59.52.

Various derivatives with different substituent groups can be synthesized according to the above synthetic method, such as G5-1 and G5-2.

Example 5

The cytidine derivative of the present example is 5-Br-4-N-(n-butoxycarbonyl)-2'-deoxy-2',2'-difluorocytidine (structural formula; 11, code: G6), whose reaction formula is as below.

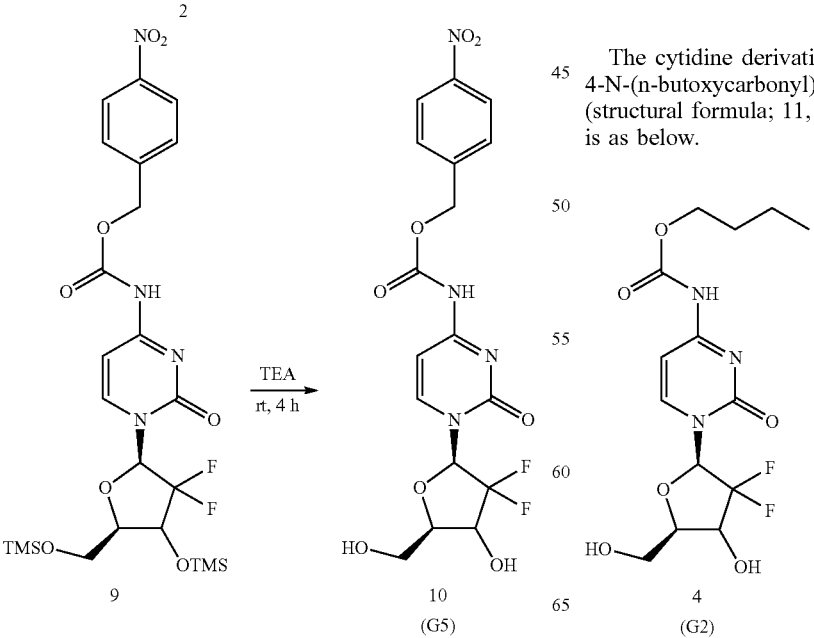

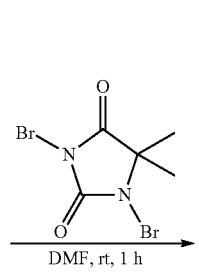

-continued

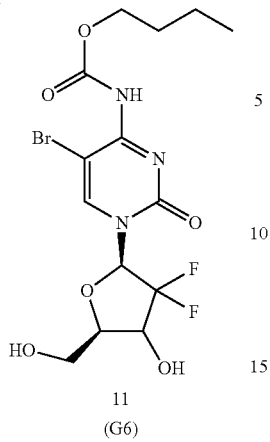

11
(G6)

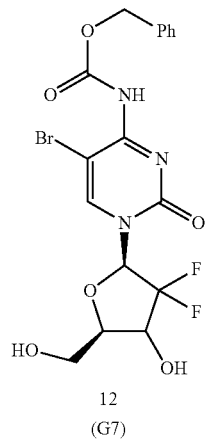

12
(G7)

After G2 was prepared according to the method of Example 1, 1 g (2.75 mmol) of G2 was dissolved in 150 mL of dimethylformamide, wherein 500 mg (1.75 mmol) of DBDMH was added while stirring. The obtained pale yellow solution was stirred, at room temperature for 1 h. According to LCMS lest, when the reaction was measured to he complete, G2 was completely transformed into G6. Rotary evaporation under reduced pressure was performed to remove solvent, and acetonitrile was used for concentrating. Silica gel chromatography was performed to purify the crude product, and 263 mg of G6 was got after the elution by dichloromethane/methanol (20:1). The total reaction yield, from G1 to G6 was 51%.

NMR characterization of G6:

$^1$H-NMR (MeOD-d$_4$, 400 MHz) δ: 8.62 (s, 1H, H5), 6.18 (t, 1H, J=6.52 Hz, H1'), 4.19 (m, 1H, H5a'), 4.15 (m, 2H, H5b', H4'), 3.95 (m, 2H, O—CH$_2$—CH$_3$), 3.17 (m, 1H, H3'), 1.36 (m, 2H, —O—CH$_2$—CH$_2$—CH$_2$—CH$_3$), 1.31 (m, 2H, —O—CH$_2$—CH$_2$—CH$_2$—CH$_3$), 0.98 (m, 2H, —O—CH$_2$—CH$_2$—CH$_2$—CH$_3$).

$^{13}$C-NMR (MeOD-d$_4$, 100 MHz) δ: 143.05, 124.56, 84.59, 81.91, 75.45, 66.17, 58.74, 58.42, 32.96, 30.64, 28.32, 18.84, 12.79, 8.17.

ESIMS: calcd for C$_{14}$H$_{18}$BrF$_2$N$_3$O$_6$ m/z 442.03 (M+H)+, found 442.02.

Example 6

The cytidine derivative of the present example is 5-Br-4-N-(carboxybenzyl)-2'-deoxy-2',2'-difluorocytidine (structural formula: 12, code: G7), whose reaction formula is as below (DMF in the reaction formula is N,N-dimethylformamide, and is the same in the following).

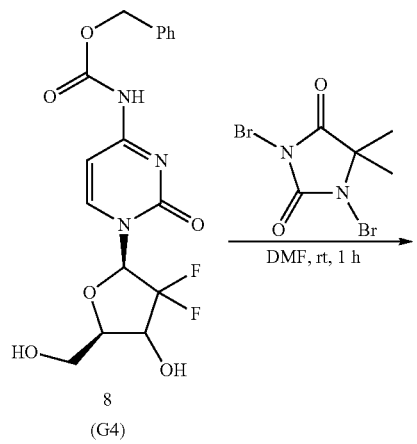

8
(G4)

After G4 was prepared according to the method of Example 3, 1 g (2.75 mmol) of G4 was dissolved in 150 mL of N, N-dimethylformamide, wherein 500 mg (1.75 mmol) of DBDMH was added while stirring. The obtained pale yellow solution was stirred for reaction at room temperature for 1 h. According to LCMS test, when the reaction was measured to be complete, G4 was completely transformed into G7. Rotary evaporation under reduced pressure was performed to remove solvent, and acetonitrile was used for concentrating. Silica gel chromatography was performed to purify the crude product, and 283 mg of G7 was got after the elution by dichloromethane/methanol (20:1). The total reaction yield from G1 to G7 was 32%.

NMR characterization of G7:

$^1$H-NMR (MeOD-d$_4$, 400 MHz) δ: 8.60 (s, 1H, H5), 7.45 (m, 2H, Ph), 7.36 (m, 3H, Ph), 6.18 (t, 1H, J=6.52 Hz, H1'), 5.24 (s, 2H, CH$_2$-Ph), 4.33 (m, 1H, H5a'), 4.0 (m, 2H, H5b', H4'), 3.81 (m, 1H, H3').

$^{13}$C-NMR (MeOD-d$_4$ 100 MHz) δ: 143.23, 135.93, 128.37, 128.27, 125.22, 122.63, 120.05, 85.41, 85.08, 84.76, 81.85, 68.77, 68.53, 68.31, 67.93, 58.76.

ESIMS: calcd for C$_{17}$H$_{16}$BrF$_2$N$_3$O$_6$ m/z 476.02 (M+H)+, found 477.09.

Similarly, after the amino group is substituted according to the synthesis route of Example 1, position 5 can be substituted by Br according to the method of Example 6 to afford G7-1 and G7-2.

According to the above preparation method, the derivatives with other groups on R2 can be prepared.

Example 7

The cytidine derivative of the present example is 5'-O-[3,5-dinitrosalicylate]-4-N-(n-butoxycarbonyl)-2'-deoxy-2',2'-difluorocytidine (structural formula: 14, code: G8).

The reaction formula is as below (in the reaction formula, (Boc)$_2$O is di-tert-butyl dicarbonate, dioxane is 1,4-dioxane, DMAP is 4-dimethylaminopyridine, EDCL is 1-(3-dimethlaminopropyl)-3-ethylcarbodiimide hydrochloride, DCM is dichloromethane, TFA is trifluoroacetic acid, and the abbreviations are the same in the following):

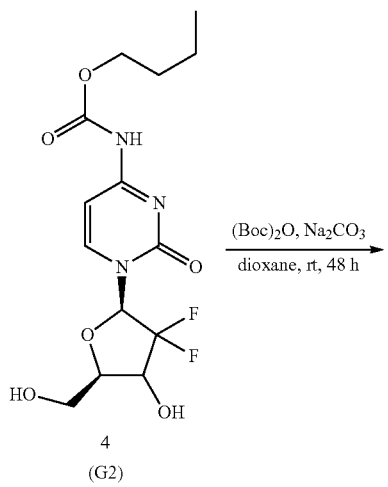

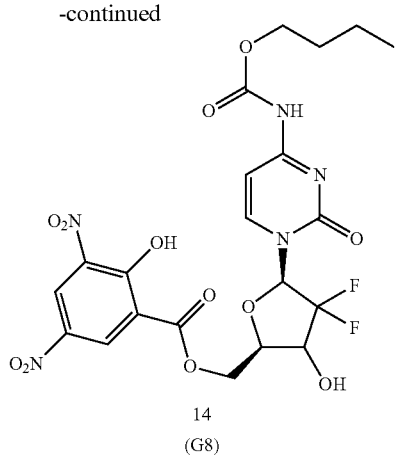

Compound 13 was prepared at first, 60 mg (0.16 mmol) of G2 prepared in Example 1 and 106 mg (1 mmol) of sodium carbonate were mixed and added to a mixed solution of 5 mL of 1,4-dioxane and water (4:1 by volume), 44 mg (0.2 mmol) of (Boc)₂O was added into the solution, stirring at 24° C. for the reaction. TLC test was performed during the reaction to determine whether G2 was completely reacted. 2 mL water was added into the system for dilution after completion of the reaction, and then extracted twice with ethyl acetate, 30 mL for each time. The organic phase obtained from extraction was sequentially washed by 5 mL of water and 5 mL of saturated saline solution, dried over anhydrous sodium sulfate after the washing was completed, and then concentrated to dryness under reduced pressure.

After the concentration, silica gel chromatography was performed for purification, and eluted with dichloromethane/acetone/methanol (1:1:0.02) to afford 51 mg of Compound 13. The yield of the above reaction was 76%.

51 mg (0.11 mmol) of the prepared Compound 13, 98 mg (0.42 mmol) of 3.5-dinitrosalicylic acid and 60 mg (0.31 mmol) of EDCL were mixed and added into 15 mL of dichloromethane. 2 mg of DMAP was added into the dichloromethane for a reaction with stirring at 24° C. for 24 hours. Thin-layer chromatography TLC test was performed during the reaction to determine whether Compound 13 was completely reacted.

After completion of the reaction, 50 mL of dichloromethane was added into the post-reaction materials, and then, 10 mL of water and 20 mL of saturated saline solution were used to wash them successively. After the completion of washing, anhydrous sodium sulfate was used for drying, concentrating till dryness. 5 mL of trifluoroacetic acid (TFA) was added into the concentrated material, and stirred at room temperature for 12 h and then concentrated till dryness. After the concentration, silica gel chromatography was performed for purification, eluted with dichloromethane/methanol (20:1) to get 18 mg of G8. The yield of reaction preparing Compound 14 from Compound 13 was 28%.

By substituting 3,5-dinitrosalicylic acid with other acids, the compound with R3 as

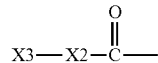

can be prepared, where X3 is phenyl ring, heterocyclic ring or fused, heterocyclic ring, as well as substitutent phenyl,

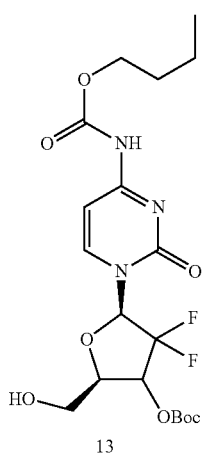

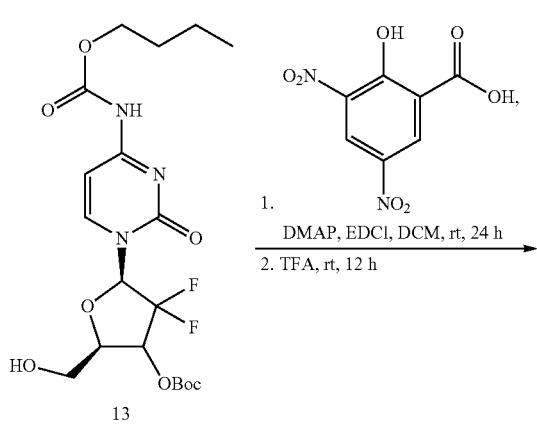

substituted heterocyclic ring or substituted fused heterocyclic ring substituted independently by one or two or three halogen, cyano, nitro, amino, hydroxyl or carboxyl; said heterocyclic ring includes imidazole, pyridine, furan, thiophene, thiazole, pyrimidine, piperazine and piperidine; said fused heterocyclic ring includes quinoline and indole: X2 is compound with $C_1$-$C_3$—$(CH_2)n$- or $C_0$-$C_3$—O—$(CH_2)n$-.

Example 8

The cytidine derivative of the present example is 5'-O-[2-(4-nitro-1H-imidazole)acetate]-4-N-(tert-butoxycarbonyl)-2'-deoxy-2',2'-difluorocytidine (structural formula: 16, code: G9).

The reaction formula is as below;

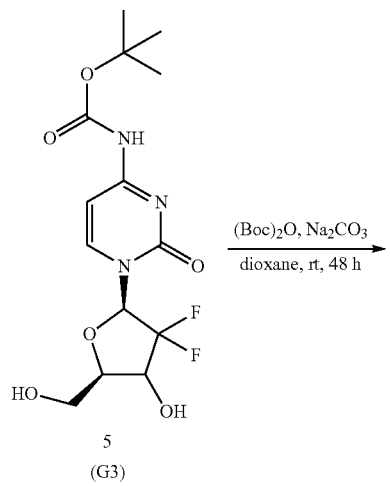

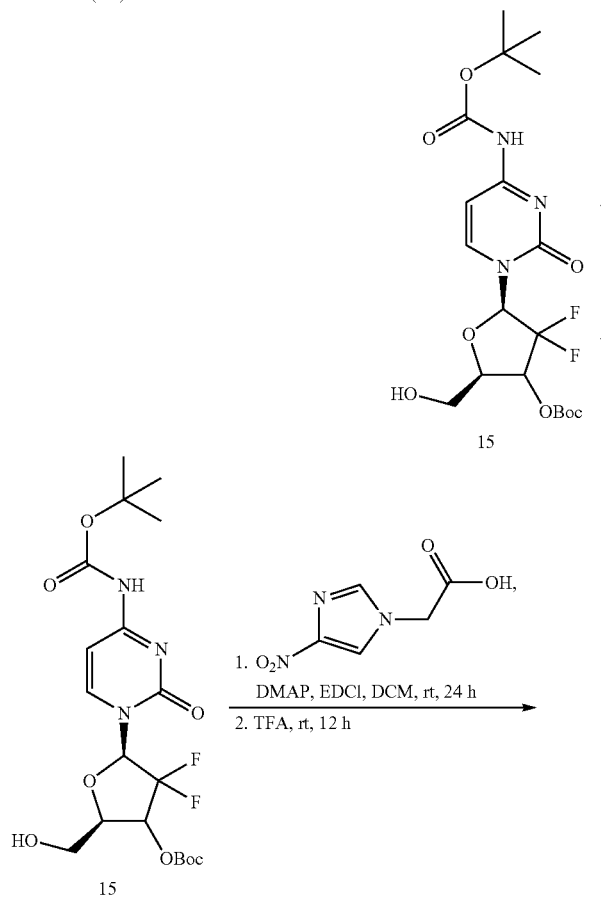

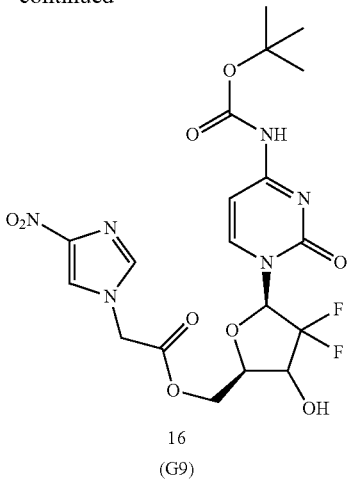

Compound 15 was prepared at first, 60 mg (0.16 mmol) of Compound 6 (G3) prepared in Example 2 and 106 mg (1 mmol) of sodium carbonate were mixed and added to a mixed solution of 5 mL of 1,4-dioxane and water (4:1 by volume). 44 mg (0.2 mmol) of (Boc)₂O was added into the solution, stirring at 24° C. for the reaction. TLC test was performed during the reaction to determine whether G2 was completely reacted. 2 mL water was added into the system, for dilution after completion of the reaction, and then extracted twice with ethyl acetate, 30 mL for each time. The organic phase obtained from extraction was sequentially washed by 5 mL of water and 5 mL of saturated saline solution, dried over anhydrous sodium sulfate after the washing was completed, and then concentrated to dryness under reduced pressure. After the concentration, silica gel chromatography was performed for purification, and eluted with dichloromethane/acetone/ethanol (1:1:0.02) to get Compound 15 of 48 mg. The yield of the above reaction was 64%.

51 mg (0.11 mmol) of the prepared Compound 15, 98 mg (0.57 mmol) of 2-(4-nitro-1H-imidazole) acetic acid and 60 mg (0.31 mmol) of EDCL were mixed and added into 15 mL of dichloromethane. 2 mg of DMAP was added into the dichloromethane for a reaction with stirring at 24° C. for 24 hours. TLC test was performed during the reaction to determine whether Compound 15 was completely reacted. After completion of the reaction, 50 mL of dichloromethane was added into the post-reaction materials, and then, 10 mL of water and 20 mL of saturated saline solution were used to wash them successively. After the completion of washing, anhydrous sodium sulfate was used for drying, concentrating till dryness. 5 mL of trifluoroacetic acid (TFA) was added into the concentrated material, and stirred at room temperature for 12 h and then, concentrated till dryness. After the concentration, silica gel chromatography was performed for purification, eluted with dichloromethane/methanol (20:1) to get 18 mg of G9. The yield of reaction preparing Compound 16 from Compound 15 was 31%.

Example 9

The cytidine derivative of the present example is coded as G10 with the following reaction formula (wherein DCC is N,N'-dicyclohexylcarbodiimide):

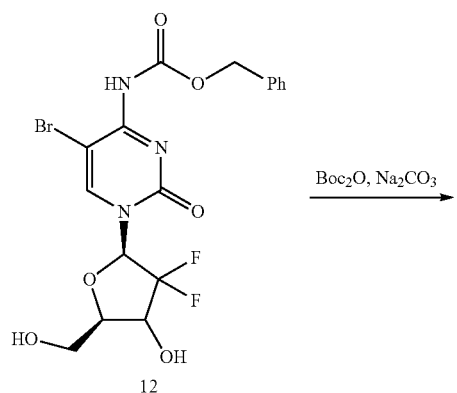

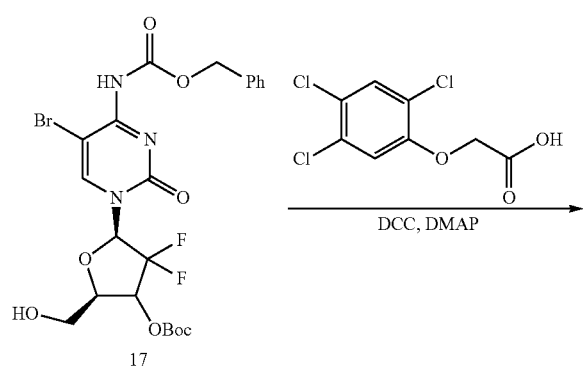

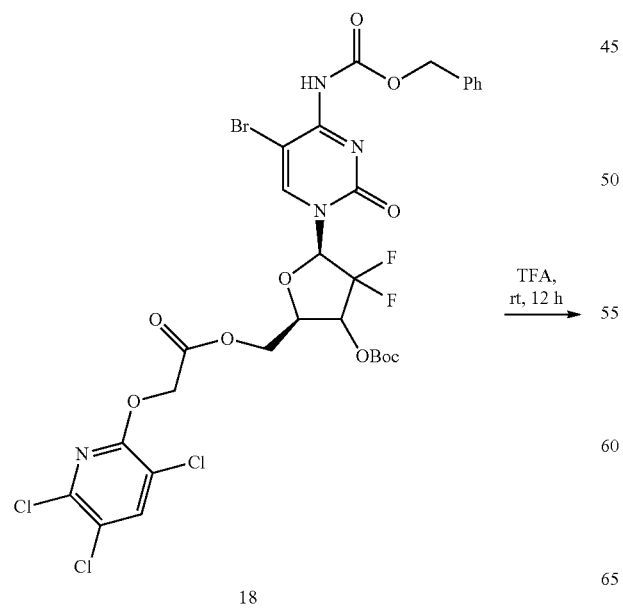

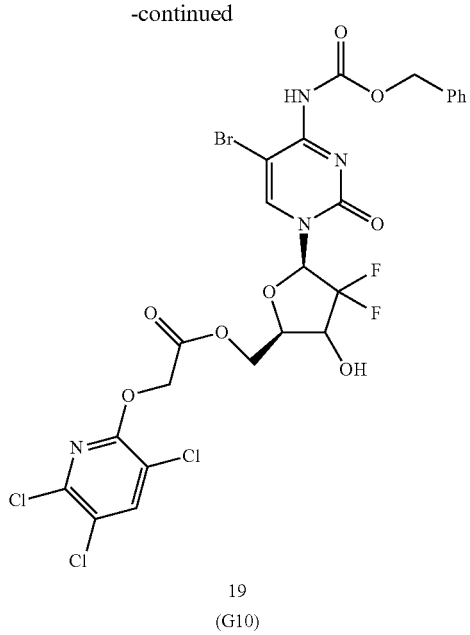

Compound 22 was prepared at first. The reaction formula is as below (wherein, DMF is N,N-dimethylformamide);

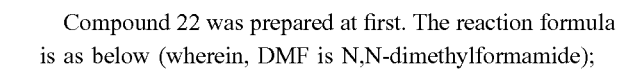

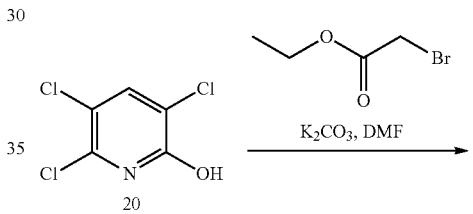

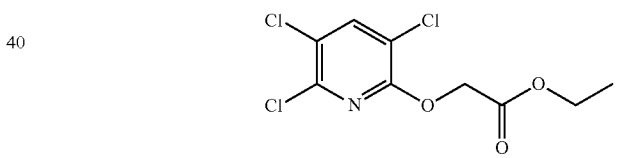

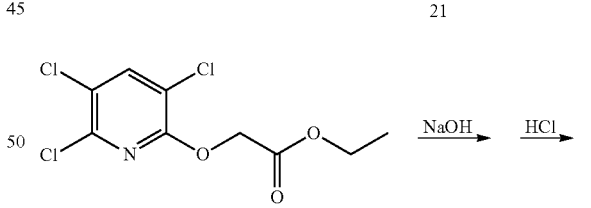

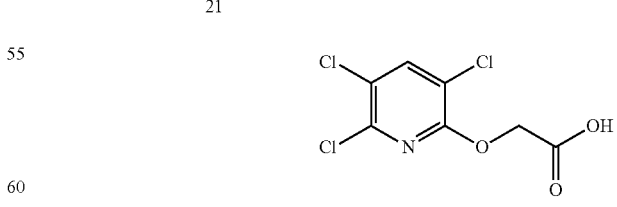

Compound 20, namely 3,5,6-trichloro-2-pyridol (5 g, 25.2 mmol), potassium carbonate (7 g, 50.6 mmol) and DMF (30 ml) were added to a reaction flask, and stirred for 15 min. After cooling to 0° C., drops of ethyl bromoacetate (2.78 ml, 25.2 mmol) was added for a reaction at room temperature for 4 h. Water (15 ml) was added and extracted with dichloromethane (15 ml×3). Rotary evaporation was performed to dry the organic phase, and the obtained Compound 21 was directly used for the next step of reaction.

Compound 21 (5.4 g, 18.8 mmol) was added into 54 mL of water, in which, sodium hydroxide (0.864 g, 21.6 mmol) was added and stirred at 80° C. for 4 h. Concentrated hydrochloric acid was dropped to adjust the pH to 1. After filtrating, 3.3 g (70%) of Compound 22 was obtained for use.

Compound 12, namely, 5-Br-4-N-(benzyloxycarbonyl)-2'-deoxy-2',2'-difluorocytidine (2 g, 4.21 mmol) and sodium carbonate (3.3 g, 31.1 mmol) were mixed and added into a system of 1,4-dioxane and water (4:1 by volume, 200 mL). (Boc)$_2$O (1.8 g, 8.25 mmol, Di-t-butyldicarbonate) was added and stirred at 25° C. for 48 h. TLC test was performed during the reaction. After the completion of reaction, 20 mL water was added for dilution, 2×100 mL of ethyl acetate was used for extraction for twice. The organic phase was washed with 50 ml, of water and 50 mL of saturated salt solution. Anhydrous sodium sulfate was used for drying and column chromatography (dichloromethane/acetone/methanol, 1:1:0.02) was performed to get Compound 17, with yield of 690 mg and 29%.

ESIMS: calcd for $C_{22}H_{24}BrF_2N_3O_8$ m/z 576.07 (M+H)+, found 576.16.

Compound 17 (350 mg, 0.61 mmol). Compound 22 (186 mg, 0.73 mmol) and DCC (250 mg, 1.21 mmol, Dicydohexylcarbodiimide, N,N'-dicyclohexylcarbodiimide) were mixed and added to 7 mL of dichloromethane, wherein, DMAP (15 mg, 0.12 mmol, 4-dimethylaminopyridine) was then added. The reaction was stirred overnight at room temperature. TLC test was performed. After completion of the reaction, 5 mL of water was added for dilution, 2×20 mL of dichloromethane was used for extraction. The organic phase was washed with 50 mL water and 50 mL of saturated salt solution. Anhydrous sodium sulfate was used for drying and column chromatography (dichloromethane/methanol, 45:1) was performed to afford Intermediate 18 (260 mg, yield: 70%). The intermediate was directly treated with TFA (trifluoroacetic acid) in dichloromethane to obtain product G10 (175 mg, yield: 77%).

NMR characterization of G10:

1H-NMR (CDCl$_3$, 400 MHz) δ 7.81 (s, 1H), 7.75 (s, 1H), 7.35 (m, 5H), 6.24 (m, 1H), 5.27 (s, 2H), 5.22 (s, 2H), 5.03 (m, 2H), 4.67 (m, 1H), 4.47 (m, 1H), 4.30 (s, 2H).

$^{13}$C NMR (CDCl$_3$, 100 MHz) δ 167.80, 162.56, 157.21, 155.57, 143.28, 140.91, 128.90, 128.78, 124.55, 123.44, 118.57, 117.47, 72.61, 68.68, 64.94, 63.83, 63.37, 62.84.

ESIMS: calcd for $C_{24}H_{18}BrCl_3F_2N_4O_8$ m/z 712.93 (M+H)+, found 712.99.

Example 10

The cytidine derivative of the present example is coded G11.

Compound 24 was prepared at first. The reaction formula is as below:

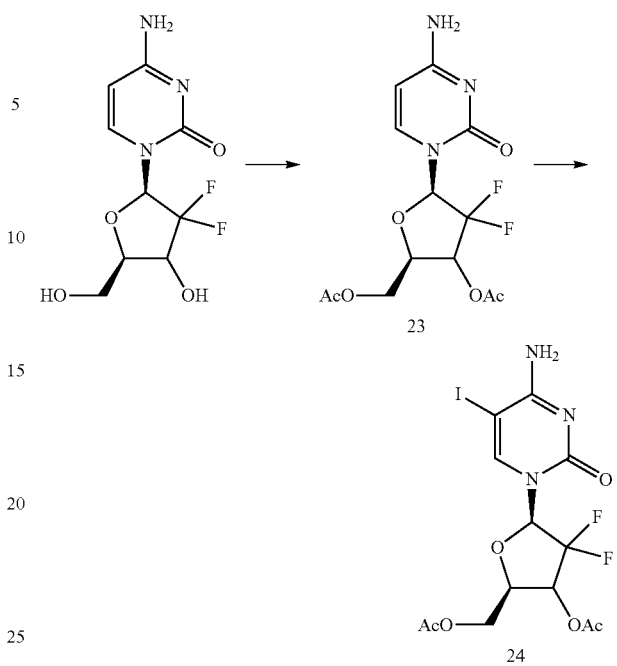

2'-deoxy-2',2'-difluorocytidine (5 g, 16 mmol) was dissolved in acetic acid (56 mL), stirred at 35° C. for 2 h; trichloromethane (1.7 mL) was added and stirred at 0° C. for 15 min. Chloroform acetyl chloride (28 ml/33 ml) was dropped into the mixed solution, stirred at 50° C. for 24 h. Rotary evaporation was performed to dry the solvent. Methanol (35 ml) was added for rotary evaporation to get the product 23 for the direct use in the next step.

Simple substance iodine (2.8 g, 11 mmol), iodic acid (0.83 g, 4.7 mmol), acetic acid (37.5 mL), carbon tetrachloride (25.5 mL), water (25.5 mL) and Compound 23 were added into a reaction flask, stirred at 40° C. for 24 h. Rotary evaporation was performed to dry the solvent. Dichloromethane and water were added. The pH was adjusted to 6-7, and the organic phase was washed with sodium thiosulfate and water. The organic phases were combined and dried with anhydrous sodium sulfate. Rotary evaporation was performed to dry the filtrate after filtrating. The obtained 5 g product of Compound 24 was to be used (the two-step yield, was 55%).

ESIMS: calcd for $C_{13}H_{14}F_2N_3O_6$ m/z 473.99 (M+H)+, found 474.14.

The reaction formula for the preparation of Compound G11 is as below;

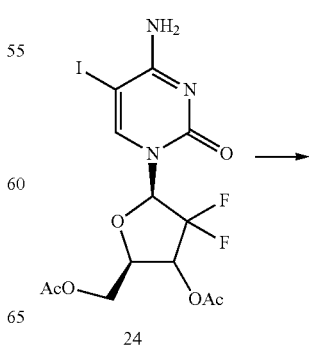

-continued

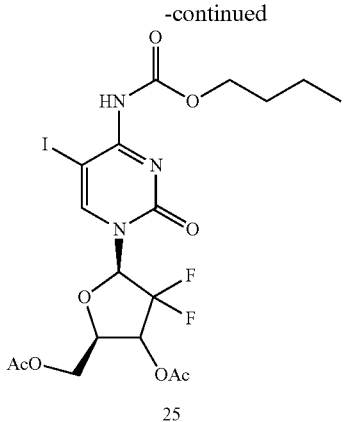

25

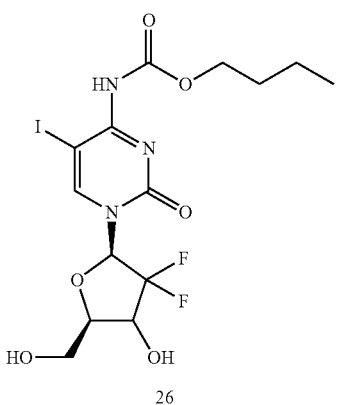

26

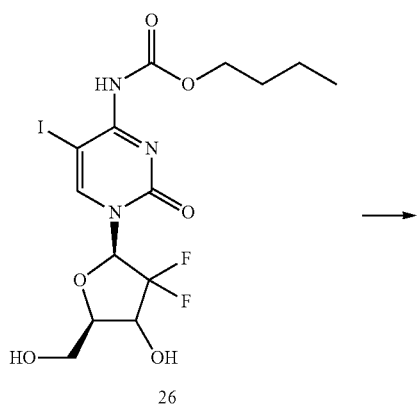

26

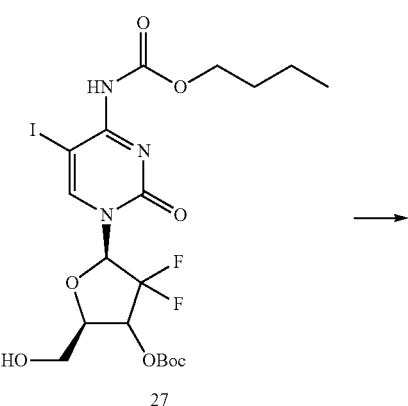

27

-continued

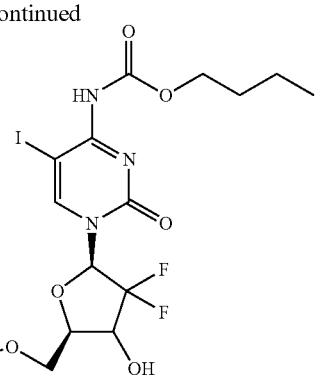

28 (G11)

Compound 24 (2.5 g, 5.3 mmol) and pyridine (1.24 g, 15.8 mmol) were dissolved in dichloromethane (35 mL), wherein butyl chloroformate (2.15 g, 15.8 mmol) was added dropwise at 0° C., and reacted at 10° C. overnight. Rotary evaporation was performed to dry the solvent. Column chromatography (dichloromethane:methanol=60:1) was performed to get 1.9 g (yield: 63%) of Compound 25.

ESIMS: calcd for $C_{18}H_{22}F_2N_3O_8$ m/z 574.04 (M+H)+, found 574.14.

Compound 25 (2.5 g, 4.3 mmol) was dissolved in methanol (40 mL) and stirred for 5 min, wherein potassium carbonate (2.1 g, 15.2 mmol) was added and stirred at room temperature overnight. Rotary evaporation was performed to dry the filtrate after filtrating and 1.5 g (yield 70.4%) of compound 26 was obtained.

ESIMS: calcd for $C_{14}H_{18}F_2N_3O_6$ m/z 490.02 (M+H)+, found 490.07.

Compound 26 (3.9 g, 8 mmol) and sodium carbonate (4.24 g, 40 mmol) were dissolved in a mixture of 1,4-dioxane (22.5 mL) and water (4.5 ml) and stirred for 10 min, wherein, di-tert-butyl dicarbonate (2.1 g, 9.6 mmol) was added, reacting at room temperature for at least 24 h. Rotary evaporation was performed to dry the solvent. Dichloromethane (70 mL) and water (100 mL) were added and dichloromethane (70 mL×3) was used for extraction. Rotary evaporation was performed to dry the organic phase. Column chromatography (dichloromethane:methanol=80:1) was performed to get 2.8 g (yield: 60%) of Compound 27.

ESIMS: calcd for $C_{19}H_{26}F_2IN_3O_8$ m/z 590.07 (M+H)+, found 590.02.

Compound 27 (50 mg, 0.61 mmol). Compound 22 (32.4 mg, 0.13 mmol) and DCC (35 mg, 0.17 mmol) were mixed and added to 2 mL of dichloromethane, wherein, DMAP (2 mg, 0.016 mmol) was then added. The reaction was stirred overnight at room temperature. TLC test was performed. After completion of the reaction, 5 mL water was added for dilution, 2×20 mL of dichloromethane was used for extraction for twice. The organic phase was washed with 5 mL water and 5 mL of saturated salt solution. Anhydrous sodium sulfate was used for drying and column chromatography (dichloromethane/methanol, 150:1) was performed to get the intermediate (50 mg, yield: 71%). The intermediate was directly treated with TFA in dichloromethane to get G11 (35 mg, yield: 80%).

The characterization of G11 is as below:

ESIMS: calcd for $C_{21}H_{20}C_{13}F_2IN_4O_8$ m/z 726.94 (M+H)+, found 727.12.

1H-NMR (MeOD-d4, 400 MHz) δ8.06 (s, 1H), 5.49 (s, 1H), 5.07 (m, 3H), 4.51 (s, 1H), 4.48 (m, 1H), 4.21 (s, 5H), 1.69 (m, 3H), 1.44 (m, 3H), 0.97 (m, 3H).

$^{13}$C-NMR (MeOD-$d_4$, 100 MHz) δ 168.06, 141.08, 140.91, 122.67, 81.73, 66.15, 63.85, 63.54, 59.38, 58.64, 33.27, 30.68, 19.73, 18.89, 15.75, 12.84, 8.78.

Example 11

The cytidine derivative of the present example is coded G12, whose reaction formula is as below:

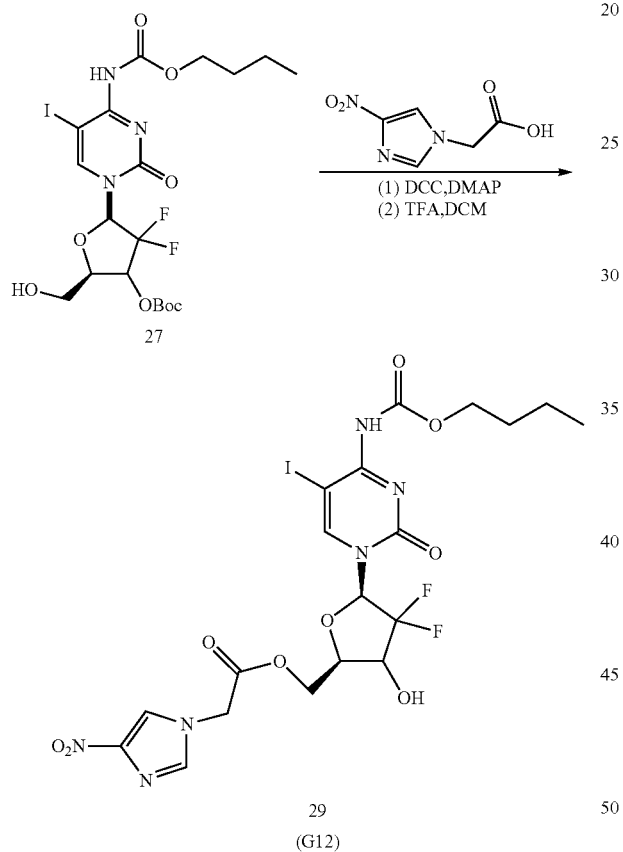

(G12)

Compound 27 (300 mg, 0.51 mmol), 2-(4-nitro-1H-imidazole) acetic acid (105 mg, 0.61 mmol) and DCC (210 mg, 1.02 mmol) were mixed and added to 10 mL of dichloromethane, wherein, DMAP (9 mg, 0.073 mmol) was then added. The reaction was stirred overnight at room temperature. TLC test was performed. After completion, of the reaction, 20 mL water was added for dilution, 3×30 mL of dichloromethane was used for extraction for three times. The organic phase was washed with 20 mL water and 20 mL of saturated salt solution. Anhydrous sodium sulfate was used, for drying and column chromatography (dicloromethane/methanol, 66:1) was performed to get 200 mg of intermediate (53%). The intermediate was directly treated with TFA in dichloromethane to get 70 mg of G12 (40%).

Example 12

The cytidine derivative of the present example is coded G13.

Compound 35 was prepared at first.

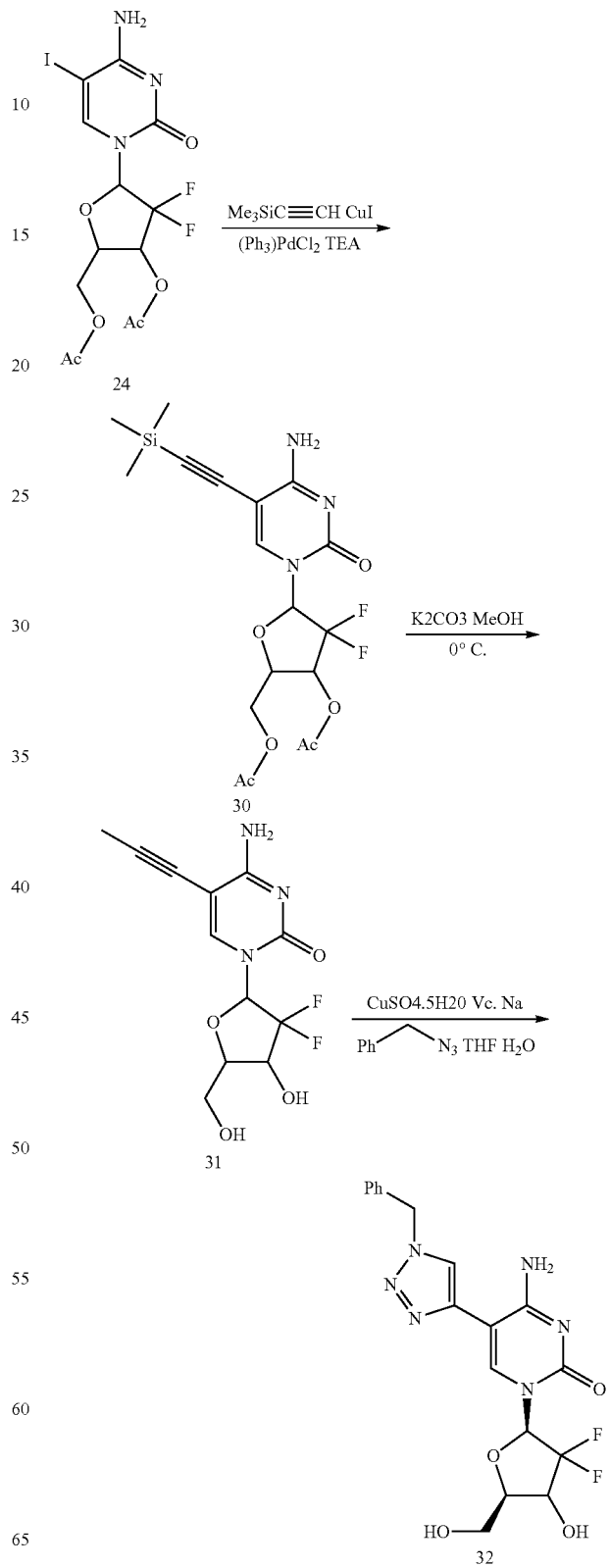

Compound 24 (5 g, 0.01 mol), (Ph$_3$) PdCl$_2$ (1.5 g, 2.14 mmol) and CuI (1.0 g, 5.27 mmol) were added to a pre-dried reaction flask, wherein, dry THF (100 ml), Me$_3$SiC≡CH (5.2 g, 0.053 mol) and TEA (15 ml) were added under nitrogen protection, reacting at room temperature overnight. After the completion of reaction, the solvent was removed by distillation under reduced pressure. Silica gel chromatography (ethyl acetate/petroleum ether: 1:1) was performed for purification to get 2.67 g (yield: 57%) of Compound 30.

Compound 30 (10 g, 1.1 mmol) was added into MeOH (200 ml), stirred till fully dissolved, and cooled at 0° C. for 15 minutes. K$_2$CO$_3$ (10.92 g, 3.95 mmol) was added and stirred at 0° C. for 2 h. After the completion of reaction, potassium carbonate was removed by filtration at first, the solvent was removed by distillation under reduced pressure. Silica gel chromatography (dichloromethane/methanol: 10:1) was performed for purification to get 5.46 g (yield: 84.27%) of Compound 31.

Compound 6.1 (5.46 g, 0.019 mol), CuSO$_4$.5H$_2$O (475 mg, 1.9 mmol) and Vc.Na (1.13 g, 5.7 mmol) were added into a mixture of THF (55 mL) and water (49 ml), and stirred under nitrogen protection at room temperature for 10 min.

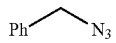

was added then, stirred under nitrogen protection at room temperature for 36 h. After the completion of reaction, the solvent was removed by distillation under reduced pressure. Silica gel chromatography (dichloromethane/methanol: 15:1) was performed for purification to get 4.88 g (yield: 61.0%) of Compound 32.

Compound 32: ESIMS: calcd for C$_{18}$H$_{18}$F$_2$N$_6$O$_4$ m/z 421.18 (M+H)+, found 421.36.

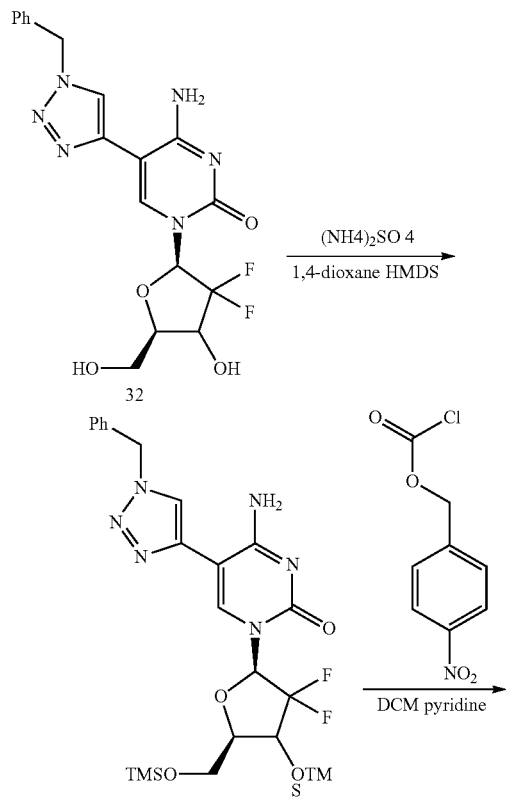

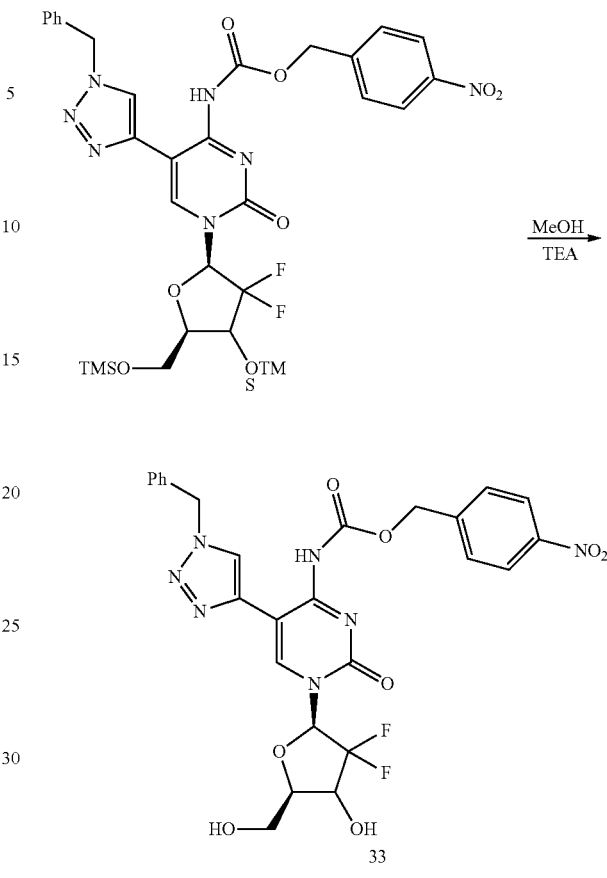

In the above reaction formula, 1,4-dioxane is 1,4-dioxane, HMDS is hexamethyldisilazane.

Compound 32 (2.0 g, 4.76 mmol), HMDS (20 mL) and (NH$_4$)$_2$SO$_4$ (50.3 mg, 0.38 mmol) were added into 1,4-dioxane (20 mL), stirred under reflux at 80° C. for 4 h. After the completion of reaction, the solvent was removed by distillation under reduced pressure. The solvent was dried by rotary evaporation with toluene (5 ml×2) and then, sucked-off by oil pump. Dichloromethane (40 ml) and pyridine (1.13 g, 14.3 mmol) were added, and the mixture was cooled to 0° C., wherein, nitrobenzoate (3.08 g, 14.3 mmol) was slowly added and stirred at 10° C. overnight. After the completion of reaction, the solvent was removed by distillation under reduced pressure. Methanol (40 mL) was added and cooled at 0° C. for 15 minutes. Then triethylamine (6.7 ml) was added dropwise, and stirred at 10° C. overnight. After the completion of reaction, the solvent was removed by distillation under reduced pressure. Silica gel chromatography (dichloromethane/methanol: 40:1) was performed for purification to get 780 mg (the three-step yield: 27.3%) of Compound 33.

Compound 33: ESIMS: calcd for C$_{26}$H$_{23}$F$_2$N$_7$O$_8$ m/z 600.22 (M+H)+, found 600.25.

33

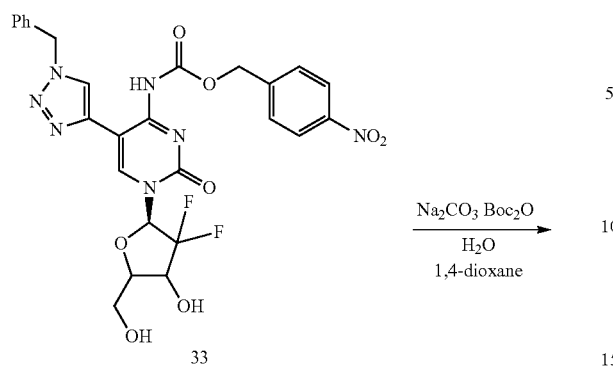

33

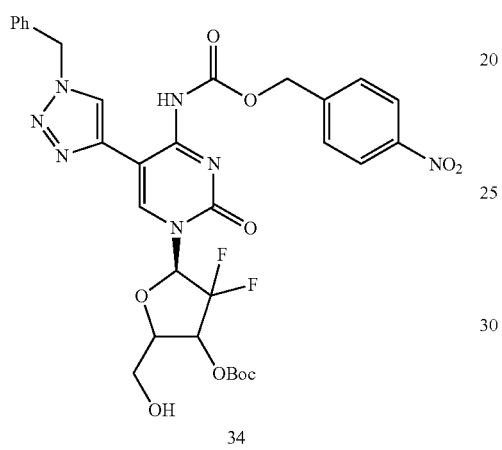

34

Boc₂O: Di-tert-butyl dicarbonate

Compound 33 (780 mg, 1.3 mmol) and Na₂CO₃ (690 mg, 6.5 mmol) were added into a mixture of 1,4-dioxane (20 ml) and water (5 ml), stirring for dissolution. (Boc)₂O (340.6 mg, 1.56 mmol) was added at room temperature and stirred overnight at room temperature. After the completion of reaction, the solvent was removed by distillation under reduced pressure. Silica gel chromatography (dichloromethane/methanol: 80:1) was performed for purification to get 366 mg (yield: 40.2%) of Compound 34.

Compound 34: ESIMS: calcd for $C_{31}H_{31}F_2N_7O_{10}$ m/z 700.28 (M+H)+, found 700.08.

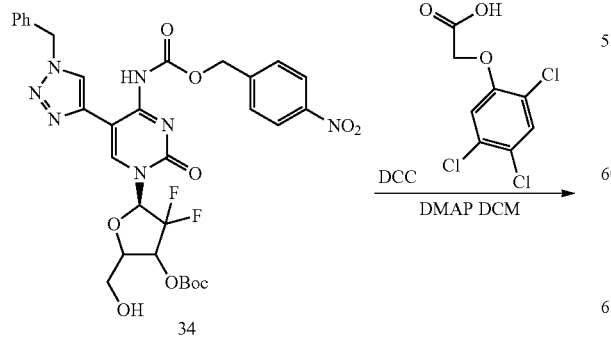

34

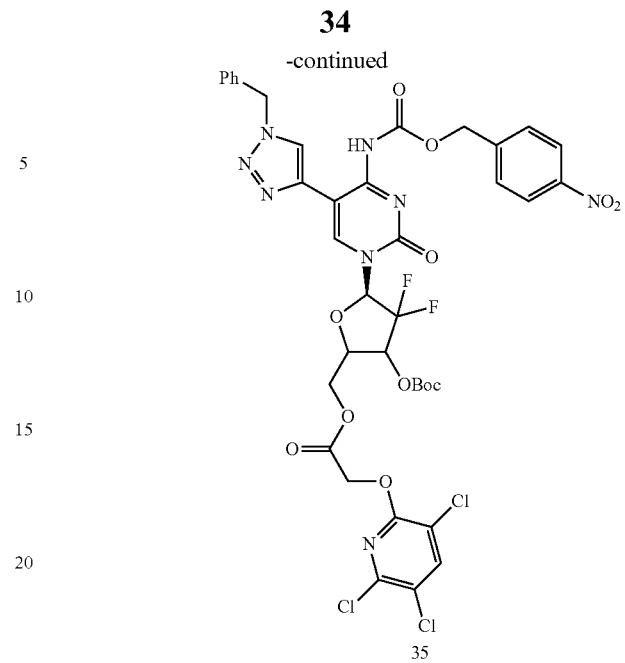

Compound 34 (250 mg, 0.36 mmol). Compound 22 (109 mg, 0.43 mmol), DCC (148 mg, 0.72 mmol) and DMAP (5 mg) were added to 12 mL of dichloromethane and stirred overnight at room temperature. After the completion of reaction, DCC was removed by suction filtration. Silica gel chromatography (dichloromethane/methanol: 100:1) was performed for purification to get 210 mg (yield: 60.0%) of Compound 35.

Compound 35: ESIMS: calcd for $C_{38}H_{33}Cl_3F_2N_8O_{12}$ m/z 937.28 (M+H)+, found 937.28.

Compound 35 (210 mg, 0.224 mmol) was added into 10 ml system of DCM/TFA=5:1 and stirred at room temperature for 4 h. After the completion of reaction, the solvent was removed by distillation under reduced pressure. Silica gel chromatography (dichloromethane/methanol: 60:1) was performed for purification to get 140 mg (yield: 75.0%) of G13.

ESIMS: calcd for $C_{33}H_{25}Cl_3F_2N_8O_{10}$ m/z 837.17 (M+H)+, found 837.27.

¹H-NMR(CDCl₃, 400 MHz) δ8.34 (s, 1H), 8.23 (m, 3H), 7.57 (m, 3H), 7.33 (m, 3H), 7.23 (m, 2H), 6.38 (m, 1H), 5.49 (m, 3H), 5.30 (s, 3H), 5.13 (m, 2H), 4.73 (m, 1H), 4.33 (m, 3H).

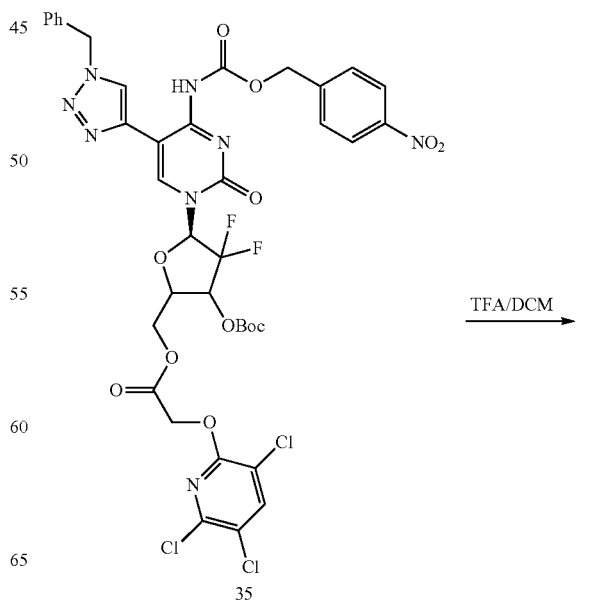

-continued

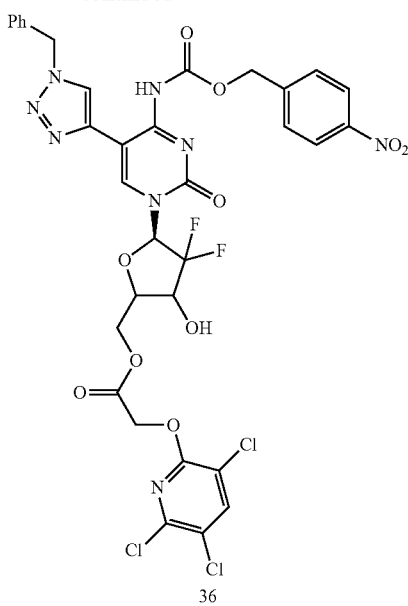

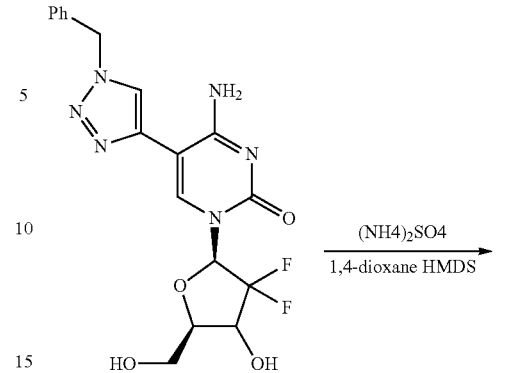

By replacing

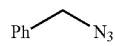

with trinitride compound that is available to purchase in the market or readily prepared, a compound having R2 as

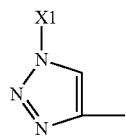

can be obtained, wherein, X1 is $C_1$-$C_{10}$ alkyl.

$C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —($CH_2$)n-Ph or substituent —($CH_2$)n-Ph; where the carbon chain on substituent alkyl and substituent alkoxy is substituted independently by one or two or three halogen, cyano, nitro, amino, hydroxyl or carboxyl; in —($CH_2$)n-Ph and substituent —($CH_2$)n-Ph, n=0, 1, 2, 3 to 10; and the carbon chain or the phenyl ring in substituent —($CH_2$)n-Ph is substituted by one or two or three H, halogen, cyano, nitro, amino, hydroxyl or carboxyl.

Example 13

The cytidine derivative of the present example was coded G14.

Compound 39 was prepared at first.

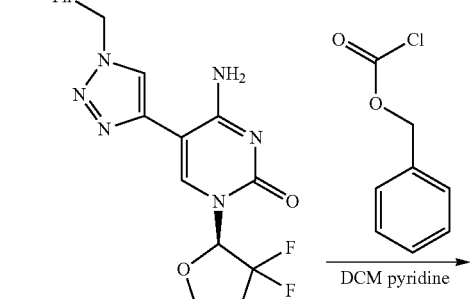

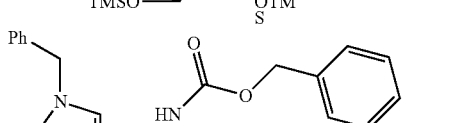

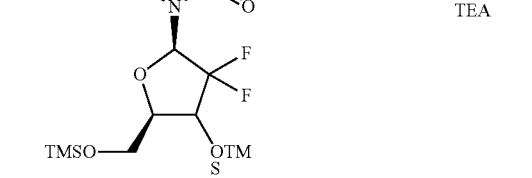

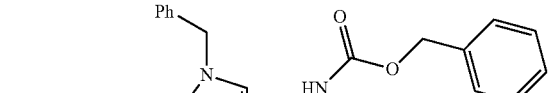

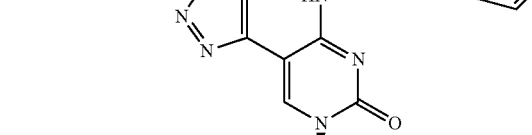

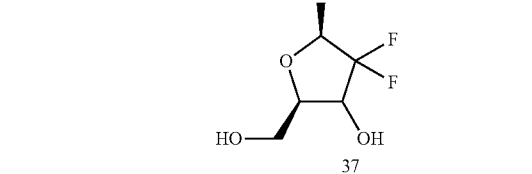

Compound 32 (1.5 g, 3.57 mmol), HMDS (15 mL) and $(NH_4)_2SO_4$ (37.7 mm, 0.285 mmol) were added into 1,4-dioxane (15 mL), and stirred, under reflux at 80° C. for 4 h. After the completion of reaction, the solvent was removed by distillation under reduced pressure. The solvent was dried by rotary evaporation with toluene (5 ml×2) and then sucked-off by oil pump. Dichloromethane (30 mL) and pyridine (0.846 g, 0.01 mmol) were added, and the mixture was cooled to 0° C., wherein, carbobenzoxy chloride (1.83 g, 0.01 mmol) was slowly added and stirred at 10° C. overnight. After the completion of reaction, the solvent was removed by distillation under reduced pressure. 40 mL, methanol was added and cooled at 0° C. for 15 minutes. Then 6 mL triethylamine was added dropwise, and stirred at 10° C. overnight. After the completion of reaction, the solvent was removed by distillation by reduced pressure. Silica gel chromatography (dichloromethane/methanol: 40:1) was performed for purification to get 570 mg (yield: 28.8%) of Compound 37.

ESIMS: calcd for $C_{25}H_{24}F_2N_6O_6$ m/z 555.24 (M+H)+, found 555.04.

Compound 37 (520 mg, 0.939 mmol) and $Na_2CO_3$ (497.5 mg, 4.69 mmol) were added into a mixture of 12 mL 1,4-dioxane and 3 ml water, and stirred for dissolution. $(Boc)_2O$ (245.5 mg, 1.126 mmol) was added at room temperature and stirred overnight at room temperature. After the completion of reaction, the solvent was removed by distillation by reduced pressure. Silica gel chromatography (dichloromethane/methanol: 80:1) was performed for purification to get 278 mg (yield: 45.3%) of Compound 38.

ESIMS: calcd for $C_{31}H_{32}F_2N_6O_8$ m/z 655.28 (M+H)+, found 655.08.

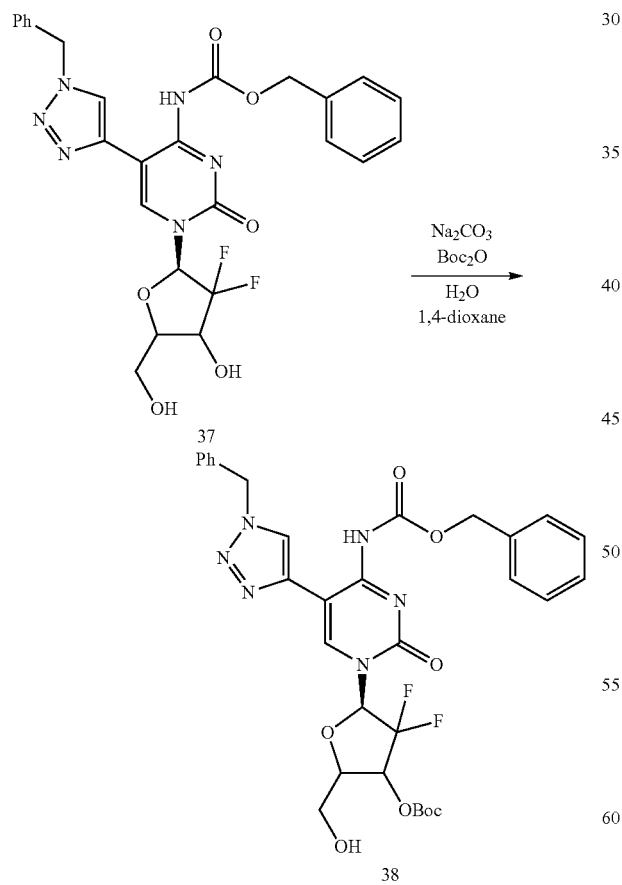

Compound 38 (200 mg, 0.3 mmol). Compound 22 (93.6 mg, 0.367 mmol). DCC (126 mg, 0.612 mmol) and DMAP (10 mg) were added into 10 mL of dichloromethane and stirred overnight at room temperature. After the completion of reaction, DCC was removed by suction filtration. Silica gel chromatography (dichloromethane/methanol: 125:1) was performed for purification to get 170 mg (yield: 62.5%) of Compound 39.

ESIMS: calcd for $C_{38}H_{34}C_{13}F_2N_7O_{10}$ m/z 914.14 (M+Na)+, found 914.36.

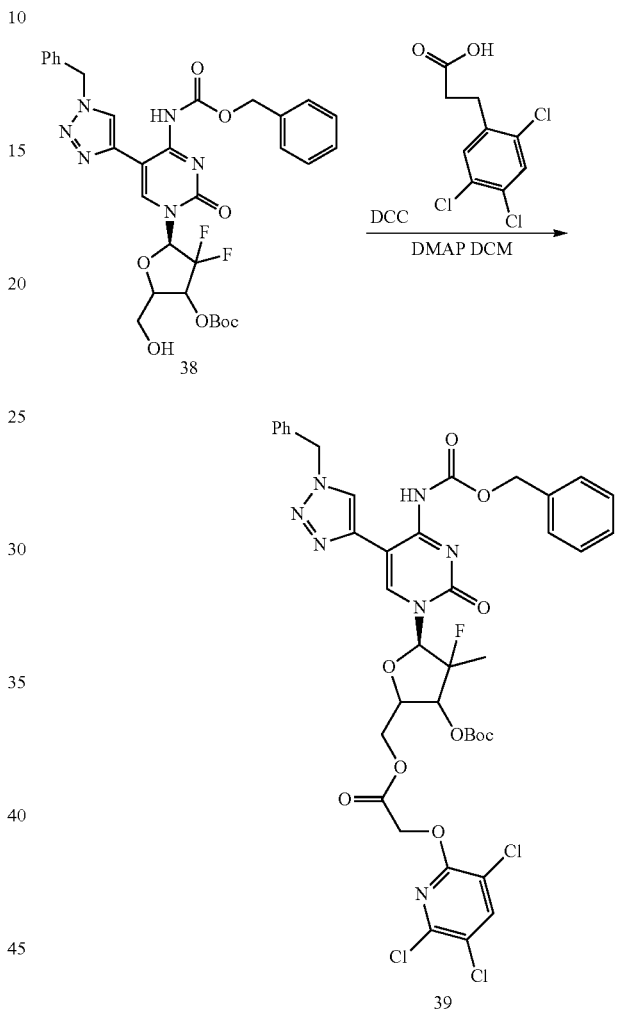

Compound 39 (140 mL, 0.157 mmol) was added into 10 mL system, of DCM/TFA=5:1 and stirred at room temperature for 4 h. After the completion of reaction, the solvent was removed by distillation by reduced pressure. Silica gel chromatography (dichloromethane/methanol: 50:1) was performed for purification to get 95 mg (yield: 76.43%) of G14.

ESIMS: calcd for calcd for $C_{33}H_{26}C_{13}F_2N_7O_8$ m/z 814.26 (M+Na)+, found 814.61.

$^1$H-NMR(CDCl$_3$ 400 MHz) δ 8.50 (s, 1H), 8.36 (s, 1H); 7.63 (s, 1H), 7.33 (m, 9H), 7.23 (m, 2H), 6.38 (m, 1H), 5.49 (m, 2H), 5.30 (s, 4H), 5.13 (m, 1H), 4.80 (m, 1H), 4.50 (m, 2H), 4.30 (m, 1H).

$^{13}$C-NMR(CDCl$_3$, 100 MHz) δ 168.61 157.65 155.68 146.20 143.22 140.59 128.87 128.02 123.07 117.24 68.19 64.11 54.40 12.69.

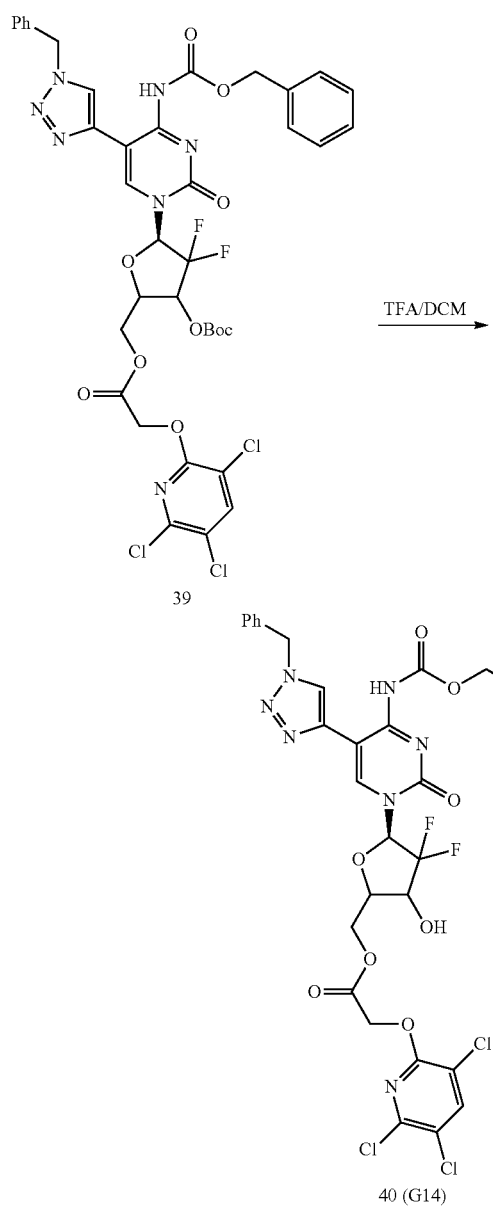

39

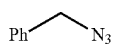

By replacing

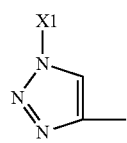

with trinitride compound that is available in the market or readily prepared, a compound having R2 as can be obtained, wherein, X1 is $C_1$-$C_{10}$ alkyl.

$C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —($CH_2$)

n-Ph or substituent —($CH_2$)n-Ph; where the carbon chain on substituent alkyl and substituent alkoxy is substituted independently by one or two or three halogen, cyano, nitre, amino, hydroxyl or carboxyl; in —($CH_2$)n-Ph and substituent —($CH_2$)n-Ph, n=0, 1, 2, 3 to 10; and the carbon chain or the phenyl ring in substituent —($CH_2$)n-Ph is substituted by one or two or three H, halogen, cyano, nitro, amino, hydroxyl or carboxyl.

Example 14

The cytidine derivative of the present example is coded G15.

Compound 43 was prepared at first.

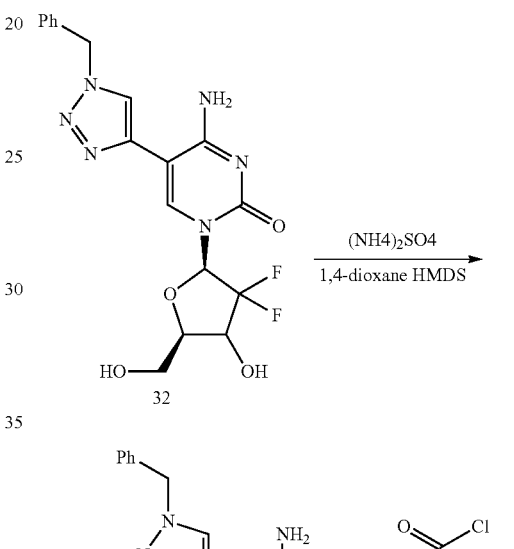

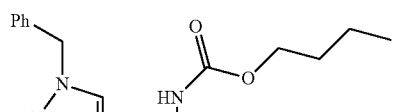

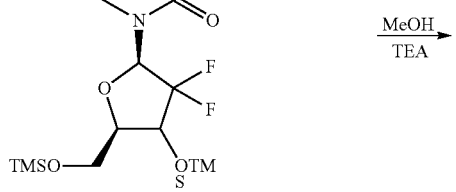

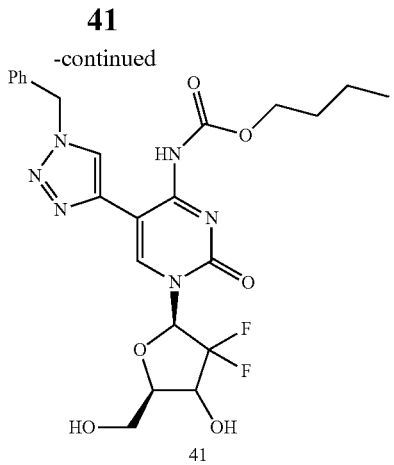

41

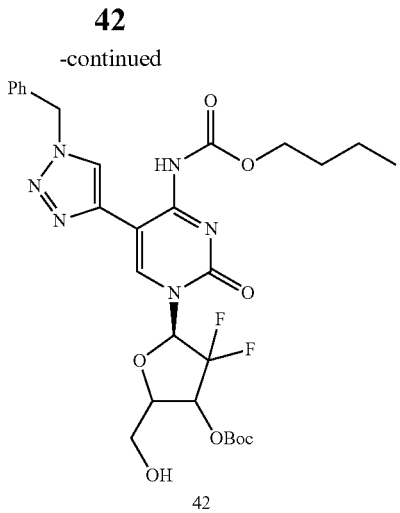

42

Compound 32 (1.3 g, 3.0 mmol), HMDS (13 mL) and (NH₄)₂SO₄ (32.7 mm, 0.247 mmol) were added into 1,4-dioxane (13 mL), and stirred under reflux at 80° C. for 4 h. After the completion of reaction, the solvent was removed by distillation by reduced pressure. The solvent was dried by rotary evaporation, with toluene (5 mL×2) and then, sucked-off by oil pump. Dichloromethane (26 mL) and pyridine (0.733 g, 9.3 mmol) were added, and the mixture was cooled to 0° C., wherein, butyl chlorocarbonate (1.268 g, 9.3 mmol) was slowly added and stirred at 10° C. overnight. After the completion of reaction, the solvent was removed by distillation by reduced pressure. Methanol (30 mL) was added and cooled at 0° C. for 15 minutes, and then triethylamine (4.5 mL) was added dropwise, and stirred at 10° C. overnight. After the completion of reaction, the solvent was removed by distillation by reduced pressure. Silica gel chromatography (dichloromethane/methanol: 40:1) was performed for purification to get 850 mg (yield: 52.8%) of Compound 41.

Compound 41 (800 mg, 1.538 mmol) and Na₂CO₃ (815 mg, 7.69 mmol) were added into a mixture of 25 mL 1,4-dioxane and 6 mL water, stirring for dissolution. (Boc)₂O (403 mg, 1.85 mmol) was added at room temperature and stirred overnight at room temperature. After the completion of reaction, the solvent was removed by distillation by reduced pressure. Silica gel chromatography (dichloromethane/methanol: 80:1) was performed for purification to get 458 mg (yield: 48.1%) of Compound 42.

ESIMS: calcd for C₂₈H₃₄F₂N₆O₈ m/z 637.76 (M+NH4)+, found 637.46.

Compound 42 (380 mg, 0.613 mmol). Compound 22 (187.5 mg, 0.736 mmol), DCC (252.5 mg, 1.226 mmol) and DMAP (20 mg) were added to 20 mL of dichloromethane and stirred overnight at room temperature. After the completion of reaction, DCC was removed by suction filtration. Silica gel chromatography (dichloromethane/methanol: 125:1) was performed for purification to get 333 mg (yield: 63.5%) of Compound 43.

ESIMS: calcd for C₃₅H₃₆C₁₃F₂N₇O₁₀ m/z 858.18 (M+H)+, found 858.28.

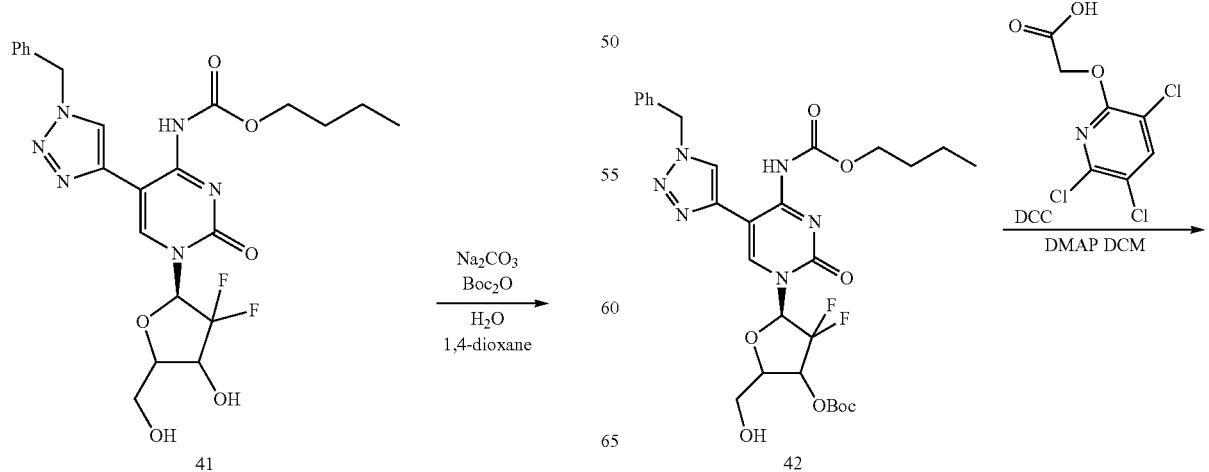

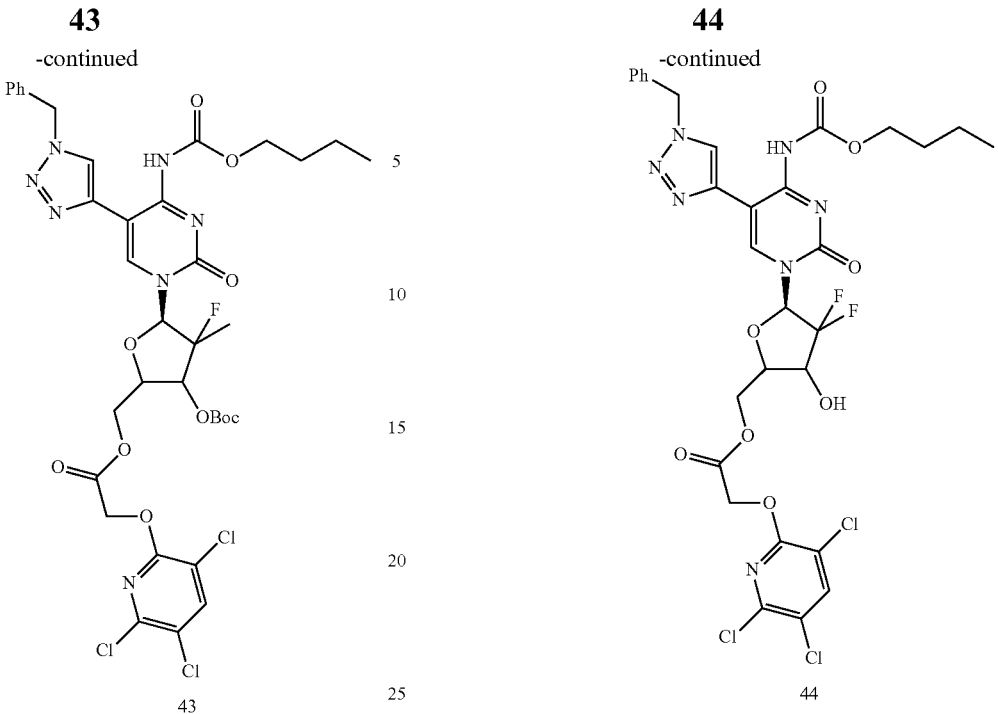

43

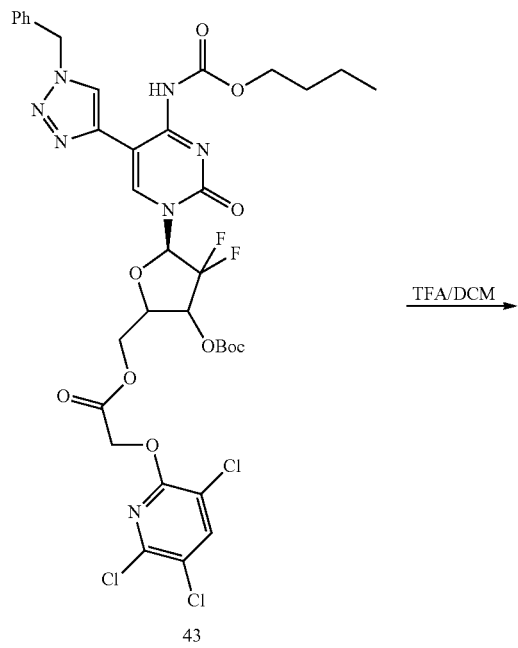

43

TFA/DCM →

44

Compound 43 (310 mg, 0.362 mmol) was added into 12 ml system of DCM/TFA=5:1 and stirred at room temperature for 4 h. After the completion of reaction, the solvent was removed by distillation by reduced pressure. Silica gel chromatography (dichloromethane/methanol: 50:1) was performed for purification to get 235 mg (yield: 85.8%) of G15.

ESIMS: calcd for $C_{30}H_{28}C_{13}F_2N_7O_8$ m/z 758.18 (M+H)+, found 758.18.

$^1$H NMR(CDCl$_3$, 400 MHz) δ8.43 (s, 1H), 8.33 (s, 1H), 8.11 (m, 1H), 7.70 (m, 1H), 7.63 (m, 1H), 7.34 (m, 4H), 6.34 (m, 1H), 5.53 (m, 3H), 5.21 (m, 2H), 4.76 (m, 1H), 4.54 (m, 1H), 4.46 (m, 1H), 4.43 (m, 1H), 4.20 (m, 2H), 1.70 (m, 2H), 1.41 (m, 2H), 0.95 (m, 3H).

By replacing with trinitride compound that is available in the market or readily prepared, a compound having R2 as can be obtained, wherein, X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —(CH$_2$)n-Ph or substituent —(CH$_2$)n-Ph; where the carbon chain on substituent alkyl and substituent alkoxy is substituted independently by one or two or three halogen, cyano, nitro, amino, hydroxyl or carboxyl; in —(CH$_2$)n-Ph and substituent —(CH$_2$)n-Ph, n=0, 1, 2, 3 to 10; and the carbon chain or the phenyl ring in substituent —(CH$_2$)n-Ph is substituted by one or two or three H, halogen, cyano, nitro, amino, hydroxyl or carboxyl.

Example 15

The cytidine derivative of the present example is coded G16.

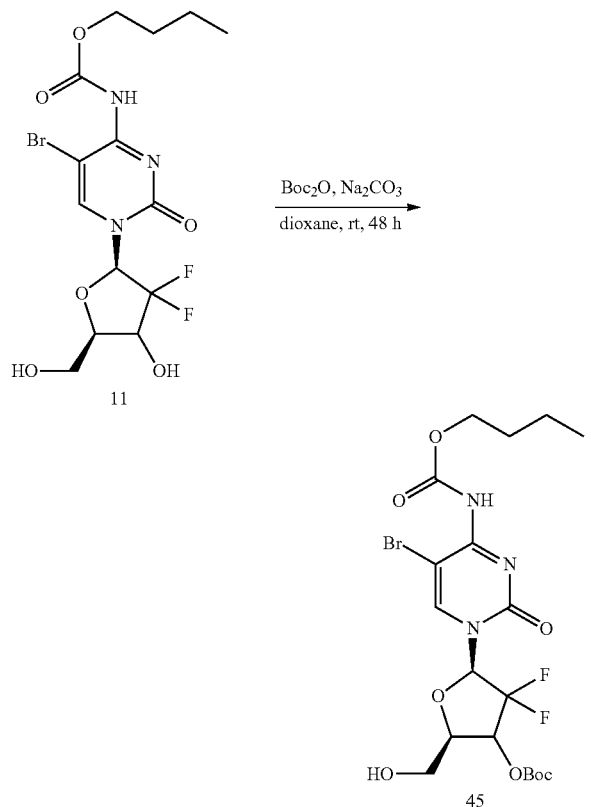

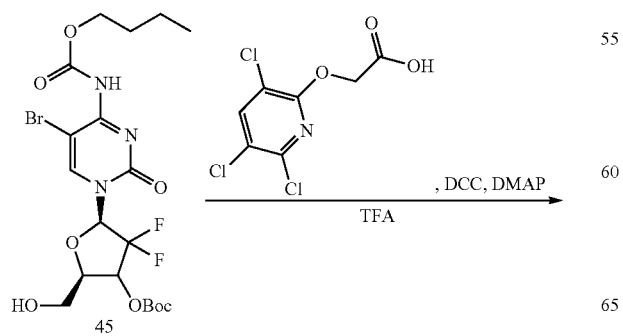

Compound 11 (2 g, 4.52 mmol) and sodium carbonate (3.4 g) were dissolved in a mixture of 133 mL 1,4-dioxane and 34 mL water and stirred for 10 min. (Boc)$_2$O (1.47 g, 6.78 mmol) was added and reacted at room temperature for at least 48 h. Rotary evaporation was performed to dry the solvent. Dichloromethane (70 mL) and water (100 mL) were added and dichloromethane (70 mL×3) was used for extraction. Rotary evaporation was performed to dry the organic phase. Column chromatography (dichloromethane:methanol=80:1) was performed to get 1.2 g (48.9%) of Compound 45.

ESIMS: calcd for C19H26BrF2N3O8 m/z 542.09 (M+H)*, found 542.11

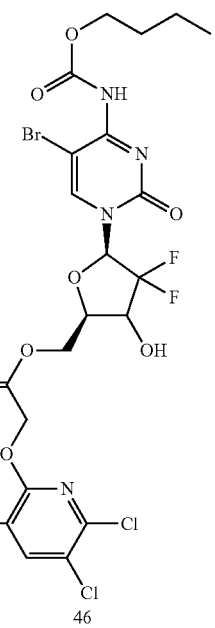

Compound 45 (355 mg, 0.65 mmol) under Boc protection, Compound 22 (499 mg, 1.95 mmol) and DCC (401 mg, 1.95 mmol) were mixed and added into 45 mL of dichloromethane, wherein, DMAP (2 mg, 0.016 mmol) was then added. The reaction was stirred overnight at room temperature. TLC test was performed. After completion of the reaction, 5 mL water was added for dilution. 2×20 mL of dichloromethane was used for extraction. The organic phase was washed with 5 mL of water and 5 mL of saturated salt solution. Anhydrous sodium sulfate was used for drying and then TFA was used to directly get target Compound G16 (110 mg, two-step yield: 24%).

$^1$H-NMR (MeOD-d$_4$, 440 MHz) δ: 8.05 (s, 2H, Ar), 6.22 (t, 1H, J=7.6 Hz, H1'), 5.15 (m, 2H), 4.67 (m, 1H, H5a'), 4.48 (m, 4H, H5b', H4', O—CH$_2$—CH$_3$), 1.70 (m, 2H, —O—CH$_2$—CH$_2$—CH$_2$—CH$_3$), 1.28 (m, 2H, —O—CH$_2$—CH$_2$—CH$_2$—CH$_3$), 0.97 (m, 2H, —O—CH$_2$—CH$_2$—CH$_2$—CH$_3$).

$^{13}$C-NMR (MeOD-d$_4$, 100 MHz) δ: 168.12, 155.98, 142.88, 141.03, 124.15, 122.75, 117.32, 82.73, 78.37, 77.97, 63.76, 63.55, 62.67, 41.82, 31.04, 30.63, 29.98, 18.88, 18.84, 12.81, 8.29.

ESIMS: calcd for C21H20BrCl3F2N4O8 m/z 681.94 (M+2H)+, found 681.15.

Example 16

The cytidine derivative of the present example is coded G17.

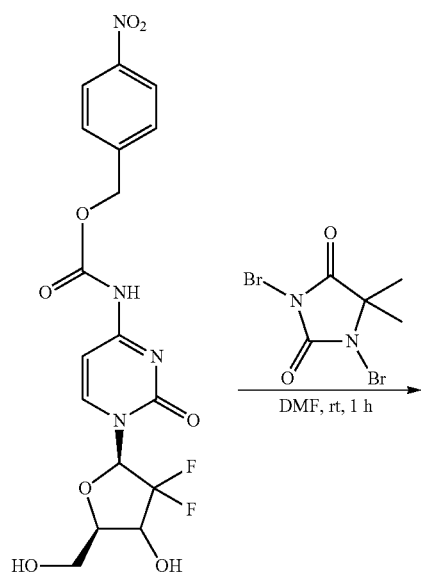

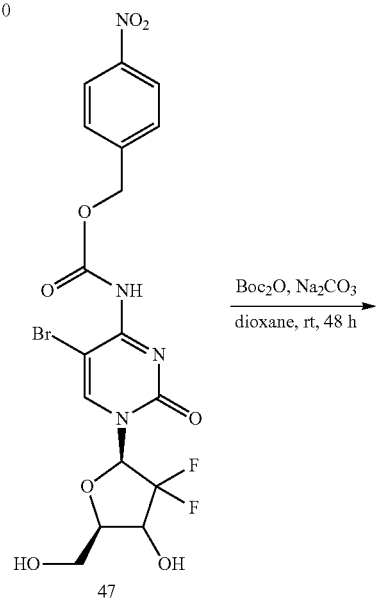

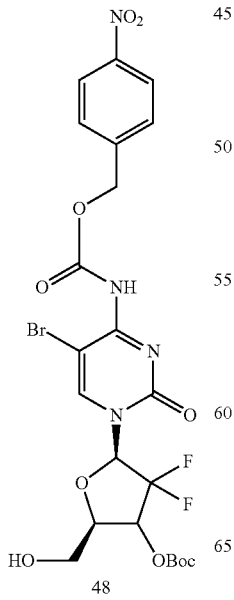

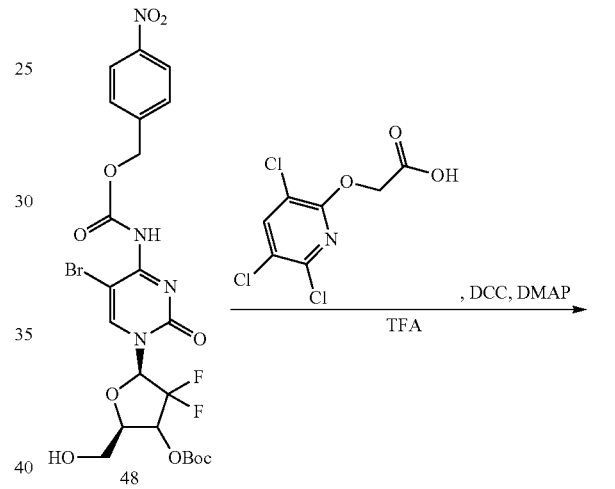

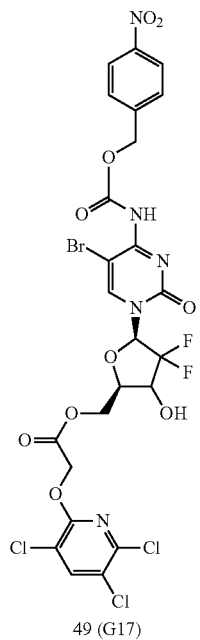

Compound 10 (911 mg, 1.75 mmol) was dissolved in 50 mL of dimethylformamide, wherein dibromohydantoin (500 mg, 1.75 mmol) was added to get faint yellow solution and stirred at room temperature for 1 h. LCMS test, was performed until, the reaction is measured to be complete. Rotary evaporation under reduced pressure was performed to remove solvent, and column chromatography (dichloromethane/methanol: 20:1) was performed to get Compound 47 (483 mg, total yield: 52.9%, white solid).

$^{1}$H-NMR(CDCl3, 400 MHz) δ 8.40 (s, 1H, Ar), 8.23 (d, J=4 Hz, 2H, Ar), 7.60 (d, J=4 Hz, 2H, Ar), 6.15 (m, 1H, H1'), 5.30 (s, 2H, Ar—CH$_2$), 4.50 (m, 1H, H5a'), 4.48 (m, 4H, H5b', H4', O—CH$_2$—CH$_3$).

Compound 47 (2.33 g, 5.72 mmol) and sodium carbonate (4.12 g) were dissolved in a mixture of 133 mL 1,4-dioxane and 34 mL water and stirred for 10 min, wherein, di-tert-butyl dicarbonate (1.72 g, 7.9 mmol) was added and reacted at room temperature for at least 48 h. Rotary evaporation was performed to dry the solvent. Dichloromethane (70 mL) and water (100 mL) were added and dichloromethane (70 mL×3) was used for extraction. Rotary evaporation was performed to dry the organic phase. Column chromatography (dichloromethane:methanol=80:1) was performed to get 1.4 g (49%) of Compound 48.

Compound 48 (540 mg, 0.869 mmol) under Boc protection. Compound 22 (667 mg, 2.60 mmol) and DCC (537 mg, 2.60 mmol) were mixed and added into 45 mL of dichloromethane, wherein, DMAP (2 mg, 0.016 mmol) was then added. The reaction was stirred overnight at room temperature. TLC test was performed. After completion, of the reaction, 5 mL water was added for dilution. 2×20 mL of dichloromethane was used for extraction. The organic phase was washed with 5 mL water and 5 mL of saturated salt solution. Anhydrous sodium sulfate was used for drying and then TFA was used to directly get target Compound G17 (115 mg, two-step yield: 17%).

$^1$H-NMR (MeOD-d$_4$, 400 MHz) δ: 0.05 (s, 2H, Ar), 6.22 (t, 1H, J=7.6 Hz, H1'), 5.15 (m, 2H), 4.67 (m, 1H, H5a'), 4.48 (m, 4H, H5b', H4', O—CH$_2$—CH$_3$), 1.70 (m, 2H, —O—CH$_2$—CH$_2$—CH$_2$—CH$_3$), 1.28 (m, 2H, —O—CH$_2$—CH$_2$—CH$_2$—CH$_3$), 0.97 (m, 2H, —O—CH$_2$—CH$_2$—CH$_2$—CH$_3$).

$^1$C-NMR (MeOD-d$_4$, 100 MHz) δ: 67.81, 157.47, 155.55, 142.93, 141.00, 128.98, 128.42, 123.99, 117.54, 79.92, 76.89, 76.55, 66.69, 65.80, 63.78, 62.54.

ESIMS: calcd for C24H17BrCl3F2N5O10 m/z 760.92 (M+2H)$^+$, found 760.10.

Example 17 Hydrochloride of Cytidine Derivative

The present example includes preparation of hydrochloride of compound of Example 1, namely 4-N-(n-butoxycarbonyl)-2'-deoxy-2',2'-difluorocytidine.

0.50 g of 4-N-(n-butoxycarbonyl)-2'-deoxy-2',2'-difluorocytidine was dissolved in 60 mL of ethyl acetate, and treated with dried hydrochloric acid gas under ice bath. After stirring for 15 min, the solvent was removed to get white solid product.

The preparation of hydrochloride salt of other cytidine derivatives was the same as the above.

In addition to the above hydrochloride, the phosphate, sulfate, carbonate, nitrate, citrate, tartrate, maleate, succinate, sulfonate, p-toluenesulfonate, mesylate, benzoate or fumarate of cytidine derivative can be prepared also.

Example 18 Freeze-Dried Powder Injection of Cytidine Derivative

The present example includes preparation of freeze-dried powder injection of Compound G14 of Example 13.

The freeze-dried powder injection of G14 included 30 g of Compound G14, 300 g of mannitol (20% w/v), 7 g of buffer agent sodium dihydrogen phosphate dihydrate, and 4.0 g of surfactant poloxamer 188 (F68).

Sodium dihydrogen phosphate dihydrate, poloxamer 188 (F68) (CAS No. 9003-11-6) and mannitol (20% w/v) weighed accurately according to the above prescription were added 300 g of water for injection that precooled to lower than 10° C., pH value of the solution was adjusted to 7.3 to 7.5 using NaOH of 0.1 mol/L. The prescription amount of G14 was then added to the above solution and well mixed; and the pH value was adjusted to 7.3±0.2 using 0.1 mol/L. NaOH solution or 0.1 mol/L HCl (7.5 was used in the present example). The result solution was added with water until 2000 g, and sterilized by filtration through 0.22 μm microporous membrane. The filtrate was dispensed into vials at 2.0 g per vial. The vials were partially stoppered, and then frozen to dryness in a freeze dryer. After the completion of drying, the vials were vacuum packed, capped, and labeled to prepare 1000 vials of lyophilized powder injections. Then, and the storage temperature was at 2 to 8° C.

In addition to the above-mentioned freeze-dried powder injection, i.e., sterile powder injection, the cytidine derivatives of the present invention can be prepared for other forms of injection, such as solution-type injection, suspension-type injection, and emulsion-type injections.

Example 19 Oral Pharmaceutical Composition of Cytidine Derivative

The pharmaceutical composition of cytidine derivative of the present example includes active ingredients and pharmaceutical necessities, in which the pharmaceutically active ingredients are cytidine derivatives or corresponding hydrochlorides prepared in the above examples. The weight of the pharmaceutically active ingredients in the composition accounted for 1% to 95% (30% in the present example). The pharmaceutical necessities consisted of water, lactose, corn starch, hydroxypropyl methyl cellulose (HPMC) and magnesium stearate. The dosage form of the pharmaceutical composition of the present example is tablet.

In terms of applicable dosage form of pharmaceutical composition, in addition to the above tablet, the pharmaceutically active ingredient can be formulated into oral powder, granule, capsule, pellet, solution, suspension, emulsion, syrup or elixir, or sustained-release and controlled-release formulations in oral administration, or other oral pharmaceutical compositions containing common corresponding pharmaceutical necessities (categorized as additives and appendages and so on, depending on their effects). For example, additives include drug grade mannitol, lactose, starch, magnesium stearate, saccharin salt, cellulose or magnesium sulfate.

In the realization of the above oral dosage forms, pharmaceutical appendages may be selected as carriers for pharmaceutically active ingredients, including those already known in the technology, such, as inert solid diluent, aqueous solvent, liposome, microsphere or/and non-toxic organic solvent, and so on. The preferred appendages include humectant, emulsifier, pH buffer, human serum albumin, antioxidant, preservative, bacteriostat, glucose, sucrose, trehalose, maltose, lecithin, glycine, sorbic acid, propene alcohol, polyethylene, protamine, boric acid, sodium chloride, or potassium chloride, mineral oil, vegetable oil and so on; one or more combinations therein may be selected as the drug carrier.

The pharmaceutical compositions of the present invention target neoplastic hematologic disorder or malignant solid tumors; specifically, target tumors include lung cancer, prostate cancer, breast cancer, colon cancer, gastric cancer, pancreatic cancer, liver cancer, esophageal cancer, brain tumors, ovarian cancer, uterine cancer, kidney cancer, head and neck cancer, skin cancer, bladder cancer, vulvar cancer, testis cancer, rectal cancer, villous cancer, germ cell tumor, malignant lymphoma, leukemia and multiple myeloma, and even more preferred target tumors may include pancreatic cancer (primary and secondary treatment), non-small cell lung cancer, breast cancer, ovarian cancer and squamous cell carcinoma of the head and neck and colon cancer. The present invention is not limited thereto.

Application Example 1, MTD Test of Single-dose Intraperitoneal Administration of a Series of Compounds on ICR Mice This experiment was to investigate the toxic effects of single-dose intraperitoneal administration on ICR mice and determine the maximum tolerated dose (MTD) of each subject. Maximum tolerated dose (MTD) refers to the dose that may not cause an animal to die, may not cause the animal to suffer weight loss exceeding 10% (compared with Day 0), or may not produce significant side effects.

1. Configuration of Test Substances.

The source of solvent used for the dissolution of test substance is as follows:

| Solvent | Lot Number | Supplier |
|---|---|---|
| Anhydrous Ethanol | 10009218 | Sinopharm Chemical Reagent Co., Ltd. |
| Cremophor EL | 27963 | Sigma |
| 0.9% Saline | 13083004 | Hua Yu Pharmaceutical Co., Ltd. |

The corresponding amount of test substance was taken in a 5 mL glass tube and dissolved in ethanol with a 5 mm magnetic stirrer for stirring. After dissolving completely, Cremophor EL was added with continuous stirring. The marked amount of saline was added and mixed evenly before use. The volume ratio of ethanol, Cremophor EL, and physiological saline was 5:5:90.

2. Test Animals

Varieties and lines: ICR mice; level: SPF; sex: female.
Source: Shanghai Slac Laboratory Animal Co., Ltd.
Certification number: 0130749.
Animal weight at the beginning of test: 18-20 g.
Quantity and sex: 41, female.
Feeding model; six per cage.
Adaptive period: 5 to 7 days, feeding conditions are the same as the test period.

The ambient temperature of animal room was 18-26° C., the relative humidity was 30-70%, and the light was on for 12 hours. The test animals had 5-7 days as adaption period prior to the test. [00148] Animal foods for growth and reproduction of SPF large and small mice were sterilized by Co60, and was purchased from Beijing Ke Ao Xie Li Co., Ltd. Sterilized filtration water was used for the test animals. During the experiment period, the animals could eat and drink freely.

3. Test Methods

Method of administration: ip. The dose was reduced in case of animal death, till an animal survived; the dose was increased in case of no animal death; the test was ended when the animals survived normally at the given high dose. Finally, the MTD of the mice on the test substances was determined according to the test results. The animals were observed continuously for 7 days after acute administration.

During the experiment, all animals were under detailed and continuous clinical observation for 14 days, twice a day (10:00 am, 16:00 pm) after administration. The observation included but not limited to: skin, hair, ear, nose, mouth, chest, abdomen, external genitalia, limbs and feet, respiratory and circulatory system, autonomic effects (such as salivation), nervous system (such as tremor, convulsions, stress response and abnormal behavior).

The body of animals was weighed before administration, and then weighed and recorded at the same time each day.

The observation results, animal body weight, and animal survival after one week of administration were recorded in detail every day.

4. Test Results

G3 and G4 could be tolerated at 350 mg/kg, G5 could be tolerated at 300 mg/kg, G6 could be tolerated at 200 mg/kg, G7 could be tolerated at 200 mg/kg, G8 could be tolerated at 300 mg/kg, G10 could be tolerated at 400 mg/kg, G11 could be tolerated at 400 mg/kg, G12 could be tolerated at 400 mg/kg, G13 could be tolerated at 400 mg/kg, G15 could be tolerated at 400 mg/kg, G16 could be tolerated at 400 mg/kg.

Application Example 2: Effects of a Series of Compounds on Tumor Growth Inhibition By observing tumor formation and growth at inoculation sites and changes in body weight of test animals, this application example evaluated tumor growth inhibition of HCT-116 colon cancer xenografts and toxicity of a single intraperitoneal injection of the compounds G2 to G17 to HCT-116 colon tumor-bearing nude mice.

1. Test Objectives

To determine the growth inhibition effect and toxicity of the cytidine derivative samples of the present invention on the transplanted tumor of nude mice bearing colon cancer HCT-116.

2. Preparation of Test Substances

The source of solvent used for the dissolution of test substance is as follows;

| Solvent | Lot | Manufacturer |
|---|---|---|
| Anhydrous Ethanol | 10009218 | Sinopharm Chemical Reagent Co., Ltd. |
| Cremophor EL | 27963 | Sigma |
| 0.9% Saline | 13083004 | Hua Yu Pharmaceutical Co., Ltd. |

The corresponding amount of test substance was taken in a 5 mL glass tube and dissolved in ethanol with a 5 mm magnetic stirrer for stirring. After dissolving completely, Cremophor EL was added with continuous stirring. The marked amount of saline was added and mixed evenly before use. The volume ratio of ethanol, Cremophor EL, and physiological saline was 5:5:90.

3. Test Animals

Varieties and lines; Balb/c Nude mice; level: SPF; sex: female.
Source: Shanghai Sippr-bk laboratory Animal Co., Ltd.
Number of animals: 100 animals were ordered, and healthy ones were chosen for the test.
Certification number for animals: 0123627.
Animal age at the beginning of test; 7-9 weeks
Animal weight at the beginning of test: 18-22 g.
Environment adapting time: 5-7 days.
Animal numbering; tail number.

The animal room was maintained at 23±2° C. 40%-70% humidity, with alternating light and dark every 12 hours.

Animal foods (SLAC-M01) were purchased from Beijing Ke Ao Xie Li Co., Ltd., and Sterilized filtration water was used for test animals. During the course of the experiment, the animals could eat and drink freely.

4. Test Methods 4.1 Tumor cells: colon cancer HCT-116 cells, purchased from the Institute of Cell Biology, Chinese Academy of Sciences. The cells were incubated by F-12 medium (containing 10% FBS) in carbon dioxide incubator at 37° C. and in saturated humidity, with 5% $CO_2$ and 95% air in volume fraction. Before inoculation, the cells at logarithmic phase were taken, and digested with 0.25% trypsin, washed once with PBS and resuspended in PBS for counting. The cells were resuspended in serum-free medium and adjusted to about $3 \times 10^7$ cell/mL.

4.2 Animal inoculation and grouping: Each nude mouse was inoculated subcutaneously with 0.1 mL of cell suspension ($3 \times 10^6$ cell/mouse) at right side of hind limb in a sterile stale. When the tumor grew to about 60-150 mm³, the nude mice with similar tumor volume and desirable shape were selected (it would be better to select single spherical shape, no irregular shape or multiple tumors grouped together) for grouping, 6 mice a group. The grouping is as follows:

| Group | Drug | Number of Animal | Dosage (mg/kg) | Method of Administration | Administration Regimen |
|---|---|---|---|---|---|
| 1 | G3 | 6 | 350 | IP | QD × 1 |
| 2 | G4 | 6 | 350 | IP | QD × 1 |
| 3 | G5 | 6 | 325 | IP | QD × 1 |
| 4 | G6 | 6 | 300 | IP | QD × 1 |
| 5 | G7 | 3 | 250 | IP | QD × 1 |
| 6 | G8 | 6 | 350 | IP | QD × 1 |
| 7 | G9 | 6 | 325 | IP | QD × 1 |
| 8 | G10 | 6 | 400 | IP | QD × 1 |
| 9 | G11 | 6 | 400 | IP | QD × 1 |
| 10 | G12 | 6 | 400 | IP | QD × 1 |
| 11 | G13 | 6 | 400 | IP | QD × 1 |
| 12 | G15 | 6 | 400 | IP | QD × 1 |
| 13 | G16 | 6 | 400 | IP | QD × 1 |
| 14 | Control | 6 | — | IP | QD × 1 |
| 15 | G1 | 6 | 400 | IP | QD × 1 |

IP: intraperitoneal injection; QD × 1: injecting once.

The control group, namely the model control group, was injected with a mixture of ethanol, Cremophor EL, and saline (5:5:90).

4.3 Animal Administration and Observation

The formations of tumor at the inoculation site of each group of nude mice were observed. The diameter of tumor nodule (D) was measured three times a week with round hole ruler, and the volume of tumor nodule (V) was calculated according to the following formula:

$$V = 3/4\pi(D/2)^3.$$

Anti-tumor activity was evaluated by tumor growth inhibition rate TGI (%) and relative tumor proliferation rate T/C (%).

The tumor growth inhibition rate TGI (%) was calculated as: TGI (%)=(Vcontrol−VTreatment)/Vcontrol×100%.

The relative tumor volume (RTV) was calculated as: RTV=Vt/V0, where V0 was the tumor volume when they were grouped and administered, and Vt was the tumor volume at the time of measurement.

The relative proliferation rate T/C (%) was calculated as: T/C (%)=$T_{RTV}$×100%.

$T_{RTV}$: RTV of the treatment group; $C_{RTV}$: RTV of the control group.

Those mice were weighed three times a week.

4.4 Clinical Symptoms

All clinical symptoms of each animal should be recorded at the beginning of the test and during the test. The observations should be made at the same time each day.

An animal would be killed by $CO_2$ when its weight loss was more than 20%, when it was about to die, or when its tumor volume exceeded 2800 mm^3. The tumor was separated and weighed, and the animal was autopsied and observed to evaluate and record whether there were pathological changes in the organs.

4.5 Data and Statistical Analysis

The data were expressed as Mean±SEM unless specially provided; Non-pairing T test was performed for the data between the two groups. P<0.05 was considered as significant difference.

5. Test Results (1) Clinical Observation and Mortality

In G4 350 mg/kg group, 1 animal died on Day 4 after administration, 3 animals had less activity, loss of body weight, and body surface temperature lower than normal and other clinical symptoms. The animals in G8 350 mg/kg group all died on Day 4 after administration. Five animals in G6, 300 mg/kg group died on Day 4 after administration. There were no significant differences in clinical symptoms in model control group and other compound groups (G3, G5, G7, G9, G10, G11, G12, G13, G15, G16). The mortality of each, group is shown in Table 2 (QD*1: single-dose intraperitoneal injection).

TABLE 2

| Group | Dosage (mg/kg) | Administration Regimen | Number | Day 22 Mortality (%) |
|---|---|---|---|---|
| G3 | 350 | QD*1 | 6 | 0 |
| G4 | 350 | QD*1 | 6 | 17 |
| G5 | 325 | QD*1 | 6 | 0 |
| G6 | 300 | QD*1 | 6 | 83 |
| G7 | 250 | QD*1 | 3 | 0 |
| G8 | 350 | QD*1 | 6 | 100 |
| G9 | 325 | QD*1 | 6 | 0 |
| G10 | 400 | QD*1 | 6 | 0 |
| G11 | 400 | QD*1 | 6 | 0 |
| G12 | 400 | QD*1 | 6 | 0 |
| G13 | 400 | QD*1 | 6 | 0 |
| G15 | 400 | QD*1 | 6 | 67 |
| G16 | 400 | QD*1 | 6 | 0 |
| Control | (NA) | QD*1 | 6 | 0 |
| G1 | 400 | QD*1 | 6 | 100 |

(2) Effects of the test compounds on body weight of mice bearing human colon cancer HCT-116.

The average weight of each group of animals is shown in Table 3.

TABLE 3

Weight of mice in G3 to G9 groups on different days.

| Group | Dosage (mg/kg) | Day 0 (g) | Day 4 (g) | Day 6 (g) | Day 8 (g) | Day 11 (g) |
|---|---|---|---|---|---|---|
| G3 | 350 | 20.47 ± 0.42 | 21.10 ± 0.41 | 21.35 ± 0.39 | 21.03 ± 0.52 | 21.43 ± 0.56 |
| G4 | 350 | 20.20 ± 0.55 | 18.22 ± 1.19 | 20.06 ± 1.18 | 20.48 ± 0.97 | 21.08 ± 0.76 |
| G5 | 325 | 21.03 ± 0.47 | 19.30 ± 0.85 | 20.82 ± 0.81 | 21.63 ± 0.62 | 22.07 ± 0.49 |
| G6 | 300 | 21.47 ± 0.65 | 19.30 ± 0.00 | 19.40 ± 0.00 | 19.60 ± 0.00 | 20.50 ± 0.00 |
| G7 | 250 | 21.63 ± 1.17 | 18.87 ± 0.09 | 20.60 ± 0.32 | 21.30 ± 0.55 | 21.97 ± 0.59 |
| G8 | 350 | 20.93 ± 0.88 | | | | |
| G9 | 325 | 20.55 ± 0.56 | 20.48 ± 0.57 | 21.02 ± 0.48 | 21.22 ± 0.51 | 21.55 ± 0.43 |
| Control | (NA) | 21.03 ± 0.73 | 20.62 ± 0.75 | 21.65 ± 0.85 | 21.50 ± 0.76 | 21.28 ± 0.86 |

TABLE 3-continued

| Group | Dosage (mg/kg) | Day 13 (g) | Day 15 (g) | Day 18 (g) | Day 20 (g) | Day 22 (g) |
|---|---|---|---|---|---|---|
| G3 | 350 | 21.75 ± 0.60 | 21.18 ± 0.66 | 21.03 ± 0.68 | 20.98 ± 0.68 | 21.17 ± 0.77 |
| G4 | 350 | 21.86 ± 0.67 | 22.10 ± 0.57 | 22.20 ± 0.43 | 22.44 ± 0.49 | 22.62 ± 0.49 |
| G5 | 325 | 22.67 ± 0.45 | 22.35 ± 0.49 | 22.75 ± 0.38 | 22.95 ± 0.50 | 23.20 ± 0.47 |
| G6 | 300 | 20.80 ± 0.00 | 20.90 ± 0.00 | 20.30 ± 0.00 | 20.20 ± 0.00 | 20.50 ± 0.00 |
| G7 | 250 | 22.80 ± 0.76 | 23.27 ± 0.93 | 23.00 ± 0.90 | 22.80 ± 1.00 | 22.60 ± 0.95 |
| G8 | 350 | | | | | |
| G9 | 325 | 22.05 ± 0.42 | 21.60 ± 0.33 | 21.17 ± 0.46 | 21.05 ± 0.36 | 22.13 ± 0.47 |
| Control | (NA) | 21.62 ± 0.84 | 21.05 ± 0.92 | 20.83 ± 0.84 | 20.82 ± 0.82 | 21.70 ± 0.90 |

Weight of mice in G10 to G16 groups on different days

| Group | Dosage (mg/kg) | Day 0 (g) | Day 1 (g) | Day 2 (g) | Day 4 (g) | Day 7 (g) |
|---|---|---|---|---|---|---|
| G10 | 400 | 19.90 ± 0.17 | 19.55 ± 0.21 | 19.73 ± 0.25 | 20.28 ± 0.19 | 20.02 ± 0.09* |
| G11 | 400 | 20.48 ± 0.27 | 19.38 ± 0.43 | 19.25 ± 0.31 | 20.07 ± 0.18 | 19.73 ± 0.17 |
| G12 | 400 | 20.05 ± 0.26 | 19.53 ± 0.36 | 19.42 ± 0.29 | 19.73 ± 0.25 | 19.85 ± 0.21 |
| G13 | 400 | 20.43 ± 0.27 | 19.05 ± 0.17* | 19.05 ± 0.35 | 19.77 ± 0.40 | 19.90 ± 0.48 |
| G15 | 400 | 20.15 ± 0.29 | 19.92 ± 0.44 | 17.9 ± 0.52** | 16.48 ± 0.77** | 20.10 ± 0.60 |
| G16 | 400 | 20.60 ± 0.23 | 20.40 ± 0.32 | 20.45 ± 0.30 | 20.62 ± 0.28 | 20.43 ± 0.27* |
| Control | (NA) | 20.55 ± 0.37 | 20.43 ± 0.45 | 20.07 ± 0.38 | 20.02 ± 0.29 | 19.33 ± 0.26 |

| Group | Dosage (mg/kg) | Day 9 (g) | Day 11 (g) | Day 14 (g) | Day 16 (g) | Day 18 (g) |
|---|---|---|---|---|---|---|
| G10 | 400 | 20.50 ± 0.24 | 20.45 ± 0.32 | 19.60 ± 0.57 | 19.47 ± 0.68 | 19.55 ± 0.70 |
| G11 | 400 | 20.43 ± 0.14 | 20.68 ± 0.20 | 20.10 ± 0.40 | 20.47 ± 0.49 | 20.80 ± 0.65 |
| G12 | 400 | 20.45 ± 0.32 | 20.70 ± 0.36 | 20.38 ± 0.32* | 20.55 ± 0.34 | 21.05 ± 0.46* |
| G13 | 400 | 20.47 ± 0.64 | 20.58 ± 0.69 | 20.53 ± 0.79 | 21.25 ± 0.94 | 21.45 ± 0.85 |
| G15 | 400 | 21.00 ± 0.10 | 21.40 ± 0.10 | 22.1 ± 0.30** | 22.75 ± 0.35** | 23.20 ± 0.50** |
| G16 | 400 | 21.03 ± 0.23** | 21.32 ± 0.26* | 20.87 ± 0.22** | 21.02 ± 0.33** | 21.80 ± 0.44** |
| Control | (NA) | 19.85 ± 0.23 | 20.23 ± 0.25 | 19.42 ± 0.19 | 19.62 ± 0.29 | 19.68 ± 0.23 |

| Group | Dosage (mg/kg) | Day 21 (g) | Day 23 (g) | Day 25 (g) | Day 28 (g) | Day 30 (g) |
|---|---|---|---|---|---|---|
| G10 | 400 | 19.47 ± 0.72 | 19.43 ± 0.78 | 19.55 ± 0.69 | 19.54 ± 0.67 | 19.55 ± 0.79 |
| G11 | 400 | 20.35 ± 0.59 | 20.23 ± 0.57 | 20.43 ± 0.63 | 20.22 ± 0.61 | 21.00 ± 1.02 |
| G12 | 400 | 20.78 ± 0.48* | 20.92 ± 0.38* | 21.38 ± 0.39* | 20.68 ± 0.31 | 20.93 ± 0.43 |
| G13 | 400 | 21.30 ± 0.81* | 21.44 ± 1.05 | 22.24 ± 1.24 | 23.08 ± 0.97 | 23.30 ± 1.07 |
| G15 | 400 | 22.40 ± 0.40** | 22.15 ± 0.45 | 22.4 ± 0.60* | 21.95 ± 0.45* | 22.40 ± 1.10 |
| G16 | 400 | 21.55 ± 0.34** | 21.78 ± 0.58* | 21.83 ± 0.59 | 21.27 ± 0.43 | 21.20 ± 0.60 |
| Control | (NA) | 19.30 ± 0.24 | 19.55 ± 0.18 | 20.08 ± 0.30 | 19.75 ± 0.05 | N/A |

*$p < 0.05$,
**$p < 0.01$ vs vehicle group

TABLE 4-1

Weight change rates of G3 to G9 groups

| Group | Dosage (mg/kg) | Day 0 (%) | Day 4 (%) | Day 6 (%) | Day 8 (%) | Day 11 (%) |
|---|---|---|---|---|---|---|
| G3 | 350 | 0.00 ± 0.00 | 3.13 ± 1.03** | 4.36 ± 0.88 | 2.86 ± 2.28 | 4.67 ± 0.64 |
| G4 | 350 | 0.00 ± 0.00 | −10.91 ± 3.45* | −1.87 ± 2.96 | 0.30 ± 1.84 | 3.85 ± 5.08 |
| G5 | 325 | 0.00 ± 0.00 | −8.40 ± 2.65* | −1.16 ± 2.31 | 2.81 ± 1.37 | 4.96 ± 1.42 |
| G6 | 300 | 0.00 ± 0.00 | 0.00 ± 0.00 | 0.52 ± 0.00 | 1.55 ± 0.00 | 6.22 ± 0.00 |
| G7 | 250 | 0.00 ± 0.00 | −12.28 ± 4.78* | −4.39 ± 3.60* | −1.24 ± 2.80 | 1.86 ± 3.24 |
| G8 | 350 | 0.00 ± 0.00 | | | | |
| G9 | 325 | 0.00 ± 0.00 | −0.08 ± 3.14 | 2.53 ± 2.85 | 3.54 ± 3.17 | 5.18 ± 2.98 |
| Control | (NA) | 0.00 ± 0.00 | −1.99 ± 0.82 | 2.88 ± 1.01 | 2.26 ± 1.32 | 1.16 ± 1.54 |

| Group | Dosage (mg/kg) | Day 13 (%) | Day 15 (%) | Day 18 (%) | Day 20 (%) | Day 22 (%) |
|---|---|---|---|---|---|---|
| G3 | 350 | 6.20 ± 0.88* | 3.40 ± 1.34 | 2.66 ± 1.40 | 2.40 ± 1.27 | 3.33 ± 2.34 |
| G4 | 350 | 7.64 ± 4.55 | 8.84 ± 4.33 | 9.28 ± 3.53* | 10.50 ± 4.03* | 11.39 ± 4.05 |
| G5 | 325 | 7.84 ± 1.39* | 6.31 ± 1.39* | 8.28 ± 1.61** | 9.18 ± 1.65** | 10.41 ± 2.03 |
| G6 | 300 | 7.77 ± 0.00 | 8.29 ± 0.00 | 5.18 ± 0.00 | 4.66 ± 0.00 | 6.22 ± 0.00 |
| G7 | 250 | 5.62 ± 2.15 | 7.71 ± 1.47 | 6.51 ± 2.30 | 5.54 ± 2.07 | 4.65 ± 2.51 |
| G8 | 350 | | | | | |

TABLE 4-1-continued

Weight change rates of G3 to G9 groups

| G9 | 325 | 7.65 ± 3.18 | 5.50 ± 3.26 | 3.38 ± 3.55 | 2.91 ± 3.85 | 8.18 ± 4.15 |
|---|---|---|---|---|---|---|
| Control | (NA) | 2.75 ± 1.27 | 0.05 ± 2.12 | −0.92 ± 2.01 | −0.93 ± 2.52 | 3.28 ± 2.98 |

*$p < 0.05$,
**$p < 0.01$ vs vehicle group

Weight change rates of G10 to G16 groups are shown in Table 4-2

TABLE 4-2

| Group | Dosage (mg/kg) | Day 0 (%) | Day 1 (%) | Day 2 (%) | Day 4 (%) | Day 7 (%) |
|---|---|---|---|---|---|---|
| G10 | 400 | 0.00 | −1.76 ± 0.49 | −0.85 ± 0.43 | 1.94 ± 0.91** | 0.61 ± 0.70** |
| G11 | 400 | 0.00 | −5.41 ± 1.27** | −6.03 ± 0.57** | −2.00 ± 0.76 | −3.58 ± 1.49 |
| G12 | 400 | 0.00 | −2.59 ± 1.08 | −3.15 ± 0.93 | −1.54 ± 1.11 | −0.93 ± 1.50* |
| G13 | 400 | 0.00 | −6.73 ± 0.73** | −6.78 ± 0.95** | −3.29 ± 1.05 | −2.67 ± 1.20 |
| G15 | 400 | 0.00 | −1.20 ± 1.02 | −11.24 ± 1.52** | −18.30 ± 3.09** | −1.96 ± 0.54 |
| G16 | 400 | 0.00 | −0.99 ± 0.59 | −0.79 ± 0.84 | −0.38 ± 1.13 | −1.73 ± 0.99* |
| Control | (NA) | 0.00 | −0.60 ± 0.59 | −2.35 ± 0.75 | −2.55 ± 0.82 | −5.85 ± 1.13 |

| Group | Dosage (mg/kg) | Day 9 (%) | Day 11 (%) | Day 14 (%) | Day 16 (%) | Day 18 (%) |
|---|---|---|---|---|---|---|
| G10 | 400 | 3.04 ± 1.24** | 2.77 ± 1.51 | −1.53 ± 2.52 | −2.19 ± 3.22 | −1.80 ± 3.13 |
| G11 | 400 | −0.18 ± 1.13 | 1.05 ± 1.44 | −1.81 ± 2.2 | 0.01 ± 2.83 | 1.66 ± 3.62 |
| G12 | 400 | 2.11 ± 2.28 | 3.34 ± 2.25 | 1.76 ± 2.11* | 2.56 ± 1.91* | 5.03 ± 2.23* |
| G13 | 400 | 0.07 ± 2.05 | 0.61 ± 2.23 | 0.35 ± 2.75 | 3.83 ± 3.60 | 4.84 ± 3.19* |
| G15 | 400 | 2.49 ± 2.01 | 4.46 ± 3.04 | 7.83 ± 1.17** | 11.00 ± 1.00* | 13.18 ± 0.32** |
| G16 | 400 | 1.99 ± 1.71* | 3.60 ± 1.31 | 1.54 ± 2.06* | 2.61 ± 2.41 | 6.99 ± 2.87* |
| Control | (NA) | −3.30 ± 1.54 | −1.39 ± 2.07 | −5.39 ± 1.69 | −4.38 ± 2.27 | −4.05 ± 2.20 |

| Group | Dosage (mg/kg) | Day 21 (%) | Day 23 (%) | Day 25 (%) | Day 28 (%) | Day 30 (%) |
|---|---|---|---|---|---|---|
| G10 | 400 | −2.23 ± 3.14 | −2.41 ± 3.42 | −1.80 ± 3.06 | −1.77 ± 2.66 | −1.95 ± 3.04 |
| G11 | 400 | −0.53 ± 3.44 | −1.07 ± 3.55 | −0.06 ± 3.97 | −1.11 ± 3.89 | 3.01 ± 7.70 |
| G12 | 400 | 3.68 ± 2.13** | 4.37 ± 1.91* | 6.69 ± 1.87* | 4.43 ± 0.69 | 5.67 ± 0.86 |
| G13 | 400 | 4.12 ± 3.07* | 5.17 ± 4.24 | 9.03 ± 4.91 | 12.25 ± 3.97 | 13.32 ± 4.25 |
| G15 | 400 | 9.29 ± 0.71** | 8.06 ± 0.44** | 9.26 ± 0.26 | 7.08 ± 0.42 | 9.20 ± 2.70 |
| G16 | 400 | 5.42 ± 2.41** | 7.14 ± 3.88 | 7.62 ± 3.76 | 3.66 ± 3.27 | 4.94 ± 2.45 |
| Control | (NA) | −5.94 ± 2.02 | −3.59 ± 1.66 | −0.97 ± 2.53 | −2.68 ± 5.27 | N/A |

*$p < 0.05$,
**$p < 0.01$ vs vehicle group

According to the above data, in terms of the growth inhibition effect of the compound on the transplanted tumor of nude mice bearing colon cancer HCT-116, the weights of animals in G4 350 mg/kg group significantly reduced on Day 4 after administration (p<0.05), with the averaged weight loss rate at 10.91±3.45%, After that, those animals had a stable growth of body weight. Their body weight significantly increased on Day 18 to Day 20 compared with model control group (p<0.05). The weights of animals in G5 325 mg/kg group significantly reduced on Day 4 after administration, with the weight loss rate less than 10%. After that, those animals had a stable growth of body weight. Their body weight significantly increased on Day 13 to Day 20 compared with model control group (p<0.05~0.01). The weights of animals in G7 250 mg/kg group significantly reduced on Day 4 and Day 6 after administration (p<0.05), with the weight loss rate at 12.28±4.78% and 4.39±3.6% respectively. After that, those animals had a stable growth of body weight. There was no significant difference in body weight between the other treated groups and the model control groups.

(3) Effects of the Test Compounds on Tumor Volume of Mice Bearing Human Colon Cancer HCT-116

The specific tumor volume in each group is shown in Table 5.

TABLE 5

Tumor volume of G3 to G9 groups

| Group | Dosage (mg/kg) | Day 0 (mm$^3$) | Day 4 (mm$^3$) | Day 6 (mm$^3$) | Day 8 (mm$^3$) | Day 11 (mm$^3$) |
|---|---|---|---|---|---|---|
| G3 | 350 | 52.61 ± 13.58** | 113.01 ± 44.54 | 180.94 ± 66.04** | 220.12 ± 86.80* | 416.66 ± 160.05 |
| G4 | 350 | 63.44 ± 18.74** | 44.53 ± 13.75** | 43.04 ± 10.69** | 43.83 ± 12.73** | 59.68 ± 11.72** |
| G5 | 325 | 65.68 ± 20.50** | 61.06 ± 22.28** | 39.01 ± 12.19** | 36.63 ± 13.03** | 44.57 ± 18.01** |
| G6 | 300 | 80.31 ± 24.42* | 47.71 ± 0.00 | 65.45 ± 0.00 | 113.10 ± 0.00 | 220.89 ± 0.00 |

TABLE 5-continued

| | Dosage (mg/kg) | Day ? | | | | |
|---|---|---|---|---|---|---|
| G7 | 250 | 133.56 ± 10.23 | 124.90 ± 18.89* | 91.30 ± 21.79** | 91.30 ± 21.79*** | 150.60 ± 38.77** |
| G8 | 350 | 41.72 ± 6.76** | | | | |
| G9 | 325 | 42.31 ± 7.52** | 51.25 ± 10.24** | 81.69 ± 23.70** | 109.19 ± 29.60** | 192.42 ± 37.84** |
| Control | (NA) | 146.28 ± 13.83 | 266.44 ± 32.36 | 422.71 ± 47.49 | 525.36 ± 66.68 | 804.17 ± 99.27 |

| Group | Dosage (mg/kg) | Day 13 (mm³) | Day 15 (mm³) | Day 18 (mm³) | Day 20 (mm³) | Day 22 (mm³) |
|---|---|---|---|---|---|---|
| G3 | 350 | 531.90 ± 203.98* | 756.53 ± 280.79 | 1004.83 ± 385.58 | 1242.64 ± 464.52 | 1390.74 ± 510.70 |
| G4 | 350 | 86.22 ± 24.86** | 140.70 ± 34.22** | 260.52 ± 51.15** | 446.16 ± 65.85** | 636.07 ± 78.89** |
| G5 | 325 | 75.90 ± 28.06** | 130.29 ± 45.17** | 235.85 ± 70.86** | 421.94 ± 104.20** | 665.68 ± 158.57** |
| G6 | 300 | 381.70 ± 0.00 | 696.91 ± 0.00 | 1436.76 ± 0.00 | 1767.15 ± 0.00 | 2144.66 ± 0.00 |
| G7 | 250 | 222.86 ± 25.56** | 384.06 ± 36.79* | 636.39 ± 30.26* | 1032.60 ± 127.82 | 1462.80 ± 246.74 |
| G8 | 350 | | | | | |
| G9 | 325 | 314.26 ± 60.92** | 553.69 ± 115.02** | 907.03 ± 187.09** | 1221.09 ± 228.29** | 1607.01 ± 297.45** |
| Control | (NA) | 1160.80 ± 173.72 | 1412.69 ± 211.72 | 1850.92 ± 266.29 | 2119.48 ± 303.08 | 2615.35 ± 352.00 |

Tumor volume of G10 to G16 groups

| Group | Dosage (mg/kg) | Day 0 (mm³) | Day 1 (mm³) | Day 2 (mm³) | Day 4 (mm³) | Day 7 (mm³) |
|---|---|---|---|---|---|---|
| G10 | 400 | 83.23 ± 12.39 | 89.33 ± 14.35** | 108.22 ± 18.22** | 154.33 ± 27.49** | 233.13 ± 37.06** |
| G11 | 400 | 71.46 ± 18.69 | 75.71 ± 22.24** | 91.91 ± 29.38** | 129.69 ± 43.49** | 200.84 ± 57.86* |
| G12 | 400 | 70.49 ± 13.19** | 68.13 ± 11.02** | 80.54 ± 15.99** | 123.31 ± 27.06** | 208.41 ± 44.11** |
| G13 | 400 | 61.03 ± 13.76* | 48.89 ± 5.84** | 52.50 ± 8.43** | 77.58 ± 16.80** | 137.02 ± 30.02** |
| G15 | 400 | 80.27 ± 13.25 | 116.82 ± 21* | 123.70 ± 25.72* | 95.41 ± 22.57** | 56.58 ± 8.87** |
| G16 | 400 | 52.57 ± 10.93** | 65.85 ± 18.30** | 97.57 ± 24.94** | 141.62 ± 45.72* | 237.57 ± 74.65* |
| Control | (NA) | 109.55 ± 8.60 | 180.51 ± 9.97 | 221.87 ± 11.44 | 296.98 ± 22.98 | 432.47 ± 39.48 |

| Group | Dosage (mg/kg) | Day 9 (mm³) | Day 11 (mm³) | Day 14 (mm³) | Day 16 (mm³) | Day 18 (mm³) |
|---|---|---|---|---|---|---|
| G10 | 400 | 393.47 ± 68.53 | 599.83 ± 84* | 996.32 ± 91.77** | 1375.20 ± 109.23** | 1636.39 ± 114.98 |
| G11 | 400 | 382.62 ± 103.38 | 495.68 ± 140.53* | 835.57 ± 194.90** | 1060.78 ± 231.28* | 1266.27 ± 242.09* |
| G12 | 400 | 300.88 ± 62.43* | 475.09 ± 105.26** | 869.70 ± 190.68* | 1267.85 ± 225.13 | 1613.91 ± 242.24 |
| G13 | 400 | 261.35 ± 79.51* | 427.82 ± 136.59** | 765.65 ± 247.40* | 1024.48 ± 288.64** | 1278.22 ± 336.74 |
| G15 | 400 | 47.71 ± 0.00** | 76.28 ± 10.83** | 200.24 ± 20.65** | 415.31 ± 33.61** | 564.86 ± 41.27** |
| G16 | 400 | 390.87 ± 115.68 | 621.03 ± 173.32 | 1038.23 ± 262.72 | 1317.52 ± 322.74 | 1566.87 ± 378.64 |
| Control | (NA) | 590.34 ± 60.83 | 976.15 ± 83.07 | 1440.15 ± 144.73 | 1811.14 ± 119.30 | 1998.33 ± 136.40 |

| Group | Dosage (mg/kg) | Day 21 (mm³) | Day 23 (mm³) | Day 25 (mm³) | Day 28 (mm³) | Day 30 (mm³) |
|---|---|---|---|---|---|---|
| G10 | 400 | 2090.18 ± 124.45 | 2120.63 ± 111.71 | 2293.73 ± 132.31 | 2404.00 ± 127.93 | 2520.69 ± 108.41 |
| G11 | 400 | 1638.64 ± 312.92 | 1678.97 ± 300.64 | 1851.89 ± 322.59 | 2126.03 ± 345.51 | 1699.56 ± 350.73 |
| G12 | 400 | 1924.26 ± 257.46 | 1943.90 ± 242.19 | 2136.52 ± 258.58 | 2040.64 ± 281.98 | 2338.31 ± 292.39 |
| G13 | 400 | 1655.72 ± 370.44 | 1425.63 ± 355.57 | 1580.18 ± 380.76 | 1485.25 ± 290.76 | 1723.43 ± 289.91 |
| G15 | 400 | 963.72 ± 58.94 | 963.72 ± 58.94 | 1086.50 ± 63.85 | 1362.50 ± 74.25 | 1767.15 ± 0.00 |
| G16 | 400 | 1877.91 ± 388.81 | 1923.55 ± 392.05 | 2110.15 ± 421.51 | 1642.01 ± 659.32 | 1323.36 ± 626.45 |
| Control | (NA) | 2444.84 ± 167.64 | 2361.69 ± 146.79 | 2582.36 ± 155.95 | 2689.30 ± 116.86 | N/A |

*$p < 0.05$,
**$p < 0.01$ vs vehicle group

According to the above data of tumor volume, the cytidine derivatives of the present invention had a significant inhibition effect on the tumor.

(4) Effects of the Test Compounds on Growth Inhibition Ratio (TGI %) of Mice Bearing Human Colon Cancer HCT-116

The effects of the test compounds on TGI % of mice bearing human colon cancer HCT-116 are shown in Table 6 below:

TABLE 6

Effects of G3-G6 on TGI % of mice bearing human colon cancer HCT-116

| Group | Dosage (mg/kg) | Day 0 (TGI %) | Day 4 (TGI %) | Day 6 (TGI %) | Day 8 (TGI %) | Day 11 (TGI %) |
|---|---|---|---|---|---|---|
| G3 | 350 | 0.00 | 57.58 | 57.20 | 58.10 | 48.19 |
| G4 | 350 | 0.00 | 83.29 | 89.82 | 91.66 | 92.58 |
| G5 | 325 | 0.00 | 77.08 | 90.77 | 93.03 | 94.46 |
| G6 | 300 | 0.00 | 82.09 | 84.52 | 78.47 | 72.53 |
| G7 | 250 | 0.00 | 53.12 | 78.40 | 82.62 | 81.27 |

TABLE 6-continued

| | | | | | |
|---|---|---|---|---|---|
| G8 | 350 | 0.00 | | | |
| G9 | 325 | 0.00 | 80.77 | 80.67 | 79.22 | 76.07 |

| Group | Dosage (mg/kg) | Day 13 (TGI %) | Day 15 (TGI %) | Day 18 (TGI %) | Day 20 (TGI %) | Day 22 (TGI %) |
|---|---|---|---|---|---|---|
| G3 | 350 | 54.18 | 46.45 | 45.71 | 41.37 | 46.82 |
| G4 | 350 | 92.57 | 90.04 | 85.93 | 78.95 | 75.68 |
| G5 | 325 | 93.46 | 90.78 | 87.26 | 80.09 | 74.55 |
| G6 | 300 | 67.12 | 50.67 | 22.38 | 16.62 | 18.00 |
| G7 | 250 | 80.80 | 72.81 | 65.62 | 51.28 | 44.07 |
| G8 | 350 | | | | | |
| G9 | 325 | 72.93 | 60.81 | 51.00 | 42.39 | 38.55 |

Effects of G10-G16 on TGI % of mice bearing human colon cancer HCT-116

| Group | Dosage (mg/kg) | Day 0 (TGI %) | Day 1 (TGI %) | Day 2 (TGI %) | Day 4 (TGI %) | Day 7 (TGI %) |
|---|---|---|---|---|---|---|
| G10 | 400 | 0.00 | 50.51 | 51.72 | 48.03 | 46.09 |
| G11 | 400 | 0.00 | 58.06 | 58.57 | 56.33 | 53.56 |
| G12 | 400 | 0.00 | 62.26 | 63.70 | 58.48 | 51.81 |
| G13 | 400 | 0.00 | 77.92 | 76.34 | 73.88 | 68.32 |
| G15 | 400 | 0.00 | 35.29 | 44.25 | 67.87 | 86.92 |
| G16 | 400 | 0.00 | 63.52 | 56.02 | 52.31 | 45.07 |

| Group | Dosage (mg/kg) | Day 9 (TGI %) | Day 11 (TGI %) | Day 14 (TGI %) | Day 16 (TGI %) | Day 18 (TGI %) |
|---|---|---|---|---|---|---|
| G10 | 400 | 33.35 | 38.55 | 30.82 | 24.07 | 18.11 |
| G11 | 400 | 35.19 | 49.22 | 41.98 | 41.43 | 36.63 |
| G12 | 400 | 49.03 | 51.33 | 39.61 | 30.00 | 19.24 |
| G13 | 400 | 55.73 | 56.17 | 46.84 | 43.43 | 36.04 |
| G15 | 400 | 91.92 | 92.19 | 86.10 | 77.07 | 71.73 |
| G16 | 400 | 33.79 | 36.38 | 27.91 | 27.25 | 21.59 |

| Group | Dosage (mg/kg) | Day 21 (TGI %) | Day 23 (TGI %) | Day 25 (TGI %) | Day 28 (TGI %) | Day 30 (TGI %) |
|---|---|---|---|---|---|---|
| G10 | 400 | 14.51 | 10.21 | 11.18 | 10.61 | 10.17 |
| G11 | 400 | 32.98 | 28.91 | 28.29 | 20.94 | 39.43 |
| G12 | 400 | 21.29 | 17.69 | 17.26 | 24.12 | 16.67 |
| G13 | 400 | 32.28 | 39.64 | 38.81 | 44.77 | 38.58 |
| G15 | 400 | 60.58 | 59.19 | 57.93 | 49.34 | 37.03 |
| G16 | 400 | 23.19 | 18.55 | 18.29 | 38.94 | 52.84 |

The TGI % of G3 350 mg/kg group reached the maximum value of 58.10% on Day 8, and was about 46.82% on Day 22. The TGI % of G4 350 mg/kg group were controlled well and reached the maximum value of 92.58% on Day 11, and kept 70% above still on Day 22. The TGI % of G5 325 mg/kg group were controlled well and reached the maximum value of 94.46% on Day 11, and kept 70% above still on Day 24. The TGI % of G9 325 mg/kg group reached the maximum value of 80.77% on Day 4, and was about 40% on Day 22. The TGI % of G7 250 mg/kg group reached the maximum value of 82.62% on Day 8, and was 44.07% on Day 22.

(5) Relative Tumor Volume (RTV) of Mice Bearing Human Colon Cancer HCT-116 and Administrated the Test Compounds Relative tumor volumes (RTV) of mice bearing human colon cancer HCT-116 and administrated Compound G3-G9 are shown in Table 7-1:

TABLE 7-1

| Group | Dosage (mg/kg) | Day 0 (RTV) | Day 4 (RTV) | Day 6 (RTV) | Day 8 (RTV) | Day 11 (RTV) |
|---|---|---|---|---|---|---|
| G3 | 350 | 1.00 ± 0.00 | 1.72 ± 0.37 | 3.21 ± 0.87 | 3.91 ± 1.20 | 7.44 ± 23.2 |
| G4 | 350 | 1.00 ± 0.00 | 0.70 ± 0.13** | 0.68 ± 0.10** | 0.69 ± 0.13** | 1.12 ± 0.29** |
| G5 | 325 | 1.00 ± 0.00 | 0.89 ± 0.17** | 0.62 ± 0.08** | 0.53 ± 0.06** | 0.60 ± 0.08** |
| G6 | 300 | 1.00 ± 0.00 | 1.42 ± 0.00 | 1.95 ± 0.00 | 3.38 ± 0.00 | 6.59 ± 0.00 |
| G7 | 250 | 1.00 ± 0.00 | 0.92 ± 0.08* | 0.66 ± 0.12** | 0.66 ± 0.12** | 1.10 ± 0.23* |
| G8 | 350 | 1.00 ± 0.00 | | | | |
| G9 | 325 | 1.00 ± 0.00 | 1.21 ± 0.16* | 1.82 ± 0.40 | 2.72 ± 0.82 | 4.91 ± 1.08 |
| Control | (NA) | 1.00 ± 0.00 | 1.88 ± 0.24 | 3.02 ± 0.40 | 3.76 ± 0.53 | 5.94 ± 1.03 |

| Group | Dosage (mg/kg) | Day 13 (RTV) | Day 15 (RTV) | Day 18 (RTV) | Day 20 (RTV) | Day 22 (RTV) |
|---|---|---|---|---|---|---|
| G3 | 350 | 8.92 ± 2.48 | 13.32 ± 4.00 | 17.04 ± 5.01 | 21.58 ± 6.58 | 24.39 ± 7.52 |
| G4 | 350 | 1.51 ± 0.39** | 2.80 ± 0.97* | 5.36 ± 1.82* | 9.65 ± 3.23 | 14.66 ± 5.30 |
| G5 | 325 | 1.04 ± 0.14** | 1.91 ± 0.35** | 3.76 ± 0.64** | 8.51 ± 3.10 | 13.37 ± 4.65 |

TABLE 7-1-continued

| | | | | | | |
|---|---|---|---|---|---|---|
| G6 | 300 | 11.39 ± 0.00 | 20.80 ± 0.00 | 42.88 ± 0.00 | 52.73 ± 0.00 | 64.00 ± 0.00 |
| G7 | 250 | 1.66 ± 0.10* | 2.91 ± 0.35* | 4.86 ± 0.65 | 7.99 ± 1.70 | 11.40 ± 2.93 |
| G8 | 350 | | | | | |
| G9 | 325 | 8.16 ± 1.87 | 13.83 ± 2.98 | 23.10 ± 5.36 | 31.85 ± 7.62 | 42.35 ± 10.48 |
| Control | (NA) | 8.60 ± 1.63 | 10.47 ± 1.99 | 13.77 ± 2.67 | 15.86 ± 3.17 | 19.45 ± 3.66 |

The relative tumor volume of G4 350 mg/kg group reduced significantly on Day 4 to Day 18 compared with the model control group (p<0.05-0.01). The relative tumor volume of G5 325 mg/kg group reduced significantly on Day 4 to Day 18 compared with the model control group (p<0.05-0.01). The relative tumor volume of G7 250 mg/kg group reduced significantly on Day 4 to Day 15 compared with the model control group (p<0.05-0.01). The relative tumor volume of G9 325 mg/kg group reduced significantly only on Day 4 compared with the model control group (p<0.05). There was no significant difference in relative tumor volume between the other treated groups and the model control groups.

Relative tumor volumes (RTV) of mice bearing human colon cancer HCT-116 and administrated G10-G16 are shown in Table 7-2:

TABLE 7-2

| Group | Dosage (mg/kg) | Day 0 (RTV) | Day 1 (RTV) | Day 2 (RTV) | Day 4 (RTV) | Day 7 (RTV) |
|---|---|---|---|---|---|---|
| G10 | 400 | 1.00 | 1.06 ± 0.12* | 1.27 ± 0.16* | 1.83 ± 0.20* | 2.82 ± 0.25 |
| G11 | 400 | 1.00 | 1.00 ± 0.13** | 1.14 ± 0.16** | 1.56 ± 0.24* | 2.68 ± 0.29* |
| G12 | 400 | 1.00 | 1.12 ± 0.22 | 1.28 ± 0.22* | 1.80 ± 0.23* | 3.07 ± 0.38 |
| G13 | 400 | 1.00 | 0.91 ± 0.12** | 0.95 ± 0.11** | 1.31 ± 0.07** | 2.39 ± 0.28* |
| G15 | 400 | 1.00 | 1.44 ± 0.12 | 1.50 ± 0.15* | 1.11 ± 0.17** | 0.88 ± 0.12* |
| G16 | 400 | 1.00 | 1.25 ± 0.20 | 2.10 ± 0.74 | 3.10 ± 1.46 | 5.12 ± 2.41 |

| Group | Dosage (mg/kg) | Day 9 (RTV) | Day 11 (RTV) | Day 14 (RTV) | Day 16 (RTV) | Day 18 (RTV) |
|---|---|---|---|---|---|---|
| G10 | 400 | 4.84 ± 0.55 | 7.60 ± 0.85 | 13.37 ± 2.23 | 18.63 ± 3.27 | 22.45 ± 4.24 |
| G11 | 400 | 5.21 ± 0.68 | 6.61 ± 0.62 | 12.40 ± 1.29 | 16.20 ± 1.72 | 20.33 ± 2.96 |
| G12 | 400 | 4.37 ± 0.50 | 7.11 ± 1.07 | 13.07 ± 2.18 | 19.45 ± 2.82 | 26.31 ± 5.44 |
| G13 | 400 | 4.07 ± 0.37 | 6.38 ± 0.77 | 11.17 ± 1.45 | 15.55 ± 1.37 | 19.86 ± 1.32 |
| G15 | 400 | 0.77 ± 0.23* | 1.19 ± 0.19* | 3.15 ± 0.61* | 6.58 ± 1.42* | 8.97 ± 2.01 |
| G16 | 400 | 8.09 ± 3.62 | 12.66 ± 5.21 | 20.81 ± 7.22 | 26.35 ± 8.64 | 31.97 ± 10.14 |

| Group | Dosage (mg/kg) | Day 21 (RTV) | Day 23 (RTV) | Day 25 (RTV) | Day 28 (RTV) | Day 30 (RTV) |
|---|---|---|---|---|---|---|
| G10 | 400 | 29.09 ± 6.00 | 29.56 ± 5.99 | 31.95 ± 6.61 | 35.86 ± 7.35 | 40.27 ± 10.35 |
| G11 | 400 | 26.21 ± 3.72 | 27.62 ± 4.39 | 30.73 ± 4.91 | 36.20 ± 6.28 | 56.36 ± 6.99 |
| G12 | 400 | 32.69 ± 8.02 | 33.10 ± 7.89 | 36.50 ± 8.74 | 43.13 ± 14.83 | 49.17 ± 15.89 |
| G13 | 400 | 26.98 ± 0.99 | 27.42 ± 1.09 | 30.60 ± 1.01 | 35.76 ± 0.97 | 42.06 ± 2.09 |
| G15 | 400 | 15.35 ± 3.61 | 15.35 ± 3.61 | 17.32 ± 4.11 | 21.75 ± 5.25 | 28.66 ± 8.38 |
| G16 | 400 | 38.61 ± 9.84 | 39.81 ± 9.58 | 43.89 ± 10.29 | 39.62 ± 10.42 | 38.70 ± 10.60 |

(6) Relative Tumor Proliferation Rate (T/C %) of Mice Bearing Human Colon Cancer HCT-116 and Administrated the Test Compounds The effects of the test compounds on T/C % of mice bearing human colon cancer HCT-116 are shown in Table 8 below;

TABLE 8-1

Effects of G3-G9 on T/C % of mice bearing human colon cancer HCT-116

| Group | Dosage (mg/kg) | Day 0 (T/C %) | Day 4 (T/C %) | Day 6 (T/C %) | Day 8 (T/C %) | Day 11 (T/C %) |
|---|---|---|---|---|---|---|
| G3 | 350 | 0.00 | 91.44 | 106.22 | 104.00 | 125.12 |
| G4 | 350 | 0.00 | 37.19 | 22.40 | 18.46 | 18.83 |
| G5 | 325 | 0.00 | 47.19 | 20.68 | 14.17 | 10.01 |
| G6 | 300 | 0.09 | 75.54 | 64.68 | 89.68 | 110.90 |
| G7 | 250 | 0.00 | 48.99 | 22.02 | 17.67 | 18.54 |
| G8 | 350 | 0.00 | | | | |
| G9 | 325 | 0.00 | 64.41 | 60.34 | 72.30 | 81.57 |

| Group | Dosage (mg/kg) | Day 13 (T/C %) | Day 15 (T/C %) | Day 18 (T/C %) | Day 20 (T/C %) | Day 22 (T/C %) |
|---|---|---|---|---|---|---|
| G3 | 350 | 103.73 | 127.18 | 123.71 | 136.12 | 125.42 |
| G4 | 350 | 17.62 | 26.72 | 38.92 | 60.84 | 75.38 |
| G5 | 325 | 12.10 | 18.26 | 27.26 | 53.67 | 68.77 |
| G6 | 300 | 132.45 | 198.59 | 311.29 | 332.56 | 329.10 |
| G7 | 250 | 19.33 | 27.80 | 35.32 | 50.40 | 58.62 |
| G8 | 350 | | | | | |
| G9 | 325 | 94.94 | 132.10 | 167.72 | 200.84 | 217.76 |

The T/C % of G4 350 mg/kg group reached the minimum value of 17.62% on Day 13, and was 75.38% on Day 22. The T/C % of G5 325 mg/kg group reached the minimum value of 10.01% on Day 11, and was 68.77% on Day 22. The T/C % of G7 250 mg/kg group reached the minimum value of 17.67% on Day 8, and was 58.62% on Day 22.

In the test about the growth inhibition effects of a series of compounds on the transplanted tumor of nude mice bearing colon cancer HCT-116, Compounds G4, G5 and G7 had good TGI % on transplanted tumor of nude mice bearing colon cancer HCT-116, with good tumor inhibition effect on Day 8 to Day 13 after single-dose intraperitoneal administration, wherein G5 reached a minimum T/C % of 10.01% on Day 11, had less effect on body-weight loss and had the average weight loss rate less than 10%.

TABLE 8-2

Effects of G10-G16 on T/C % of mice bearing human colon cancer HCT-116

| Group | Dosage (mg/kg) | Day 0 (T/C %) | Day 1 (T/C %) | Day 2 (T/C %) | Day 4 (T/C %) | Day 7 (T/C %) |
|---|---|---|---|---|---|---|
| G10 | 400 | 0.00 | 63.00 | 61.29 | 66.28 | 69.09 |
| G11 | 400 | 0.00 | 59.32 | 55.14 | 56.59 | 65.48 |
| G12 | 400 | 0.00 | 66.60 | 61.57 | 65.24 | 75.07 |
| G13 | 400 | 0.00 | 54.25 | 45.65 | 47.27 | 58.47 |
| G15 | 400 | 0.00 | 85.43 | 72.40 | 40.26 | 21.43 |
| G16 | 400 | 0.00 | 74.29 | 101.15 | 112.20 | 125.35 |

| Group | Dosage (mg/kg) | Day 9 (T/C %) | Day 11 (T/C %) | Day 14 (T/C %) | Day 16 (T/C %) | Day 18 (T/C %) |
|---|---|---|---|---|---|---|
| G10 | 400 | 86.30 | 82.36 | 96.62 | 107.93 | 117.59 |
| G11 | 400 | 92.89 | 71.69 | 89.59 | 93.88 | 106.51 |
| G12 | 400 | 77.79 | 77.05 | 94.48 | 112.70 | 137.82 |
| G13 | 400 | 72.57 | 69.19 | 80.76 | 90.09 | 104.04 |
| G15 | 400 | 13.79 | 12.86 | 22.77 | 38.11 | 46.97 |
| G16 | 400 | 144.20 | 137.25 | 150.39 | 152.70 | 167.46 |

| Group | Dosage (mg/kg) | Day 21 (T/C %) | Day 23 (T/C %) | Day 25 (T/C %) | Day 28 (T/C %) | Day 30 (T/C %) |
|---|---|---|---|---|---|---|
| G10 | 400 | 124.28 | 149.49 | 147.80 | 169.72 | 162.31 |
| G11 | 400 | 111.97 | 139.68 | 142.15 | 171.30 | 227.13 |
| G12 | 400 | 139.66 | 167.43 | 168.82 | 204.13 | 198.17 |
| G13 | 400 | 115.26 | 138.66 | 141.56 | 169.23 | 169.53 |
| G15 | 400 | 65.58 | 77.64 | 80.11 | 102.92 | 115.51 |
| G16 | 400 | 164.95 | 201.32 | 203.01 | 187.50 | 155.98 |

Based on the results of the above tests, it was confirmed that the new type of cytidine derivative of the present invention provided excellent effects as antitumor agent.

The above examples illustrate the present invention well and those technical staff in this field understand that various modifications may be made and those modifications are within the scope of the present invention.

What is claimed is:

1. A cytidine derivative, having the following general formula (I):

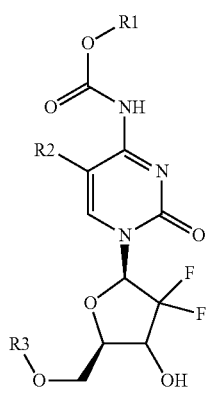

wherein, R1 is $C_1$-$C_{10}$ alkyl, $C_1$-$C_{10}$ substituent alkyl, —(CH$_2$)n-Ph, or substituent —(CH$_2$)n-Ph; wherein in said —(CH$_2$)n-Ph, n=0, 1, 2, 3 to 10, Ph is phenyl; a carbon chain of said substituent alkyl is independently substituted by one or two or three halogen, cyano group, nitro group, amino group, hydroxyl group or carboxyl group; in said substituent —(CH$_2$)n-Ph, n=0, 1, 2, 3 to 10, and a carbon chain or a phenyl ring of which is independently substituted by one or two or three halogen, cyano group, nitro group, amino group, hydroxyl group or carboxyl group;

R2 is halogen or a structure denoted as

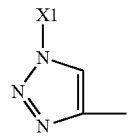

in which a line with a loose end indicating an attachment point, wherein X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —(CH$_2$)n-Ph, or substituent —(CH$_2$)n-Ph; wherein a carbon chain of said substituent alkyl is substituted independently by one or two or three halogen, cyano group, nitro group, amino group, hydroxyl group or carboxyl group; a carbon chain of said substituent alkoxy is substituted independently by one or two or three halogen, cyano group, nitro group, amino group, hydroxyl group or carboxyl group; in said —(CH$_2$)n-Ph, n=0, 1, 2, 3 to 10; in said substituent —(CH$_2$)n-Ph, n=0, 1, 2, 3 to 10, and a carbon chain or a phenyl ring of which is substituted by one or two or three H, halogen, cyano group, nitro group, amino group, hydroxyl group or carboxyl group;

R3 is H or

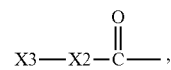

wherein X3 is phenyl ring, heterocyclic ring, fused heterocyclic ring, substituent phenyl that is substituted independently by one or two or three halogen, cyano group, nitro group, amino group, hydroxyl group or carboxyl group, substituent heterocyclic ring that is substituted independently by one or two or three halogen, cyano group, nitro group, amino group, hydroxyl group or carboxyl group, or substituent fused heterocyclic ring that is substituted independently by one or two or three halogen, cyano group, nitro group, amino group, hydroxyl group or carboxyl group; wherein said heterocyclic ring is imidazole, pyridine, furan, thiophene, thiazole, pyrimidine, piperazine or piperidine; said fused heterocyclic ring is quinoline or indole; and X2 is —(CH$_2$)n-, wherein n=1, 2, 3, or X2 is —O—(CH$_2$)n-, wherein n=0, 1, 2, 3.

2. The new cytidine derivative according to claim 1, wherein R3 is not H.

3. The cytidine derivative according to claim 1, wherein X1 is —(CH$_2$)n-Ph or substituent —(CH$_2$)n-Ph.

4. The cytidine derivative according to claim 3, wherein: R1 is $C_1$-$C_4$ alkyl, $C_1$-$C_4$ substituent alkyl, benzyl, or substituent benzyl; X3 of R3 is substituent imidazole substituted independently by one or two or three halogen, cyano group, nitro group, amino group, hydroxyl group or carboxyl group, substituent pyridine substituted independently by one or two or three halogen, cyano group, nitro group, amino group, hydroxyl group or carboxyl group, or substituent phenyl ring substituted independently by one or two or three halogen, cyano group, nitro group, amino group, hydroxyl group or carboxyl group.

5. A method of inhibiting tumor, comprising: administering to a subject with a therapeutically effective amount of a cytidine derivative or a pharmaceutically acceptable salt form thereof, wherein the cytidine derivative has the following general formula (I):

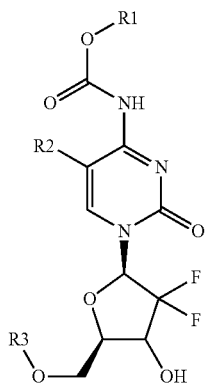

wherein, R1 is $C_1$-$C_{10}$ alkyl, $C_1$-$C_{10}$ substituent alkyl, —(CH$_2$)n-Ph, or substituent —(CH$_2$)n-Ph; wherein in said —(CH$_2$)n-Ph, n=0, 1, 2, 3 to 10, Ph is phenyl; a carbon chain of said substituent alkyl is independently substituted by one or two or three halogen, cyano group, nitro group, amino group, hydroxyl group or carboxyl group; in said substituent —(CH$_2$)n-Ph, n=0, 1, 2, 3 to 10, and a carbon chain or a phenyl ring of which is independently substituted by one or two or three halogen, cyano group, nitro group, amino group, hydroxyl group or carboxyl group;

R2 is halogen or a structure denoted as

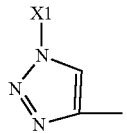

in which a line with a loose end indicating an attachment point, wherein X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —(CH$_2$)n-Ph, or substituent —(CH$_2$) n-Ph; wherein a carbon chain of said substituent alkyl is substituted independently by one or two or three halogen, cyano group, nitro group, amino group, hydroxyl group or carboxyl group; a carbon chain of said substituent alkoxy is substituted independently by one or two or three halogen, cyano group, nitro group, amino group, hydroxyl group or carboxyl group; in said —(CH$_2$)n-Ph, n=0, 1, 2, 3 to 10; in said substituent —(CH$_2$)n-Ph, n=0, 1, 2, 3 to 10, and a carbon chain or a phenyl ring of which is substituted by one or two or three H, halogen, cyano group, nitro group, amino group, hydroxyl group or carboxyl group; and R3 is H or

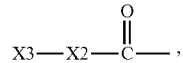

wherein X3 is phenyl ring, heterocyclic ring, fused heterocyclic ring, substituent phenyl that is substituted independently by one or two or three halogen, cyano group, nitro group, amino group, hydroxyl group or carboxyl group, substituent heterocyclic ring that is substituted independently by one or two or three halogen, cyano group, nitro group, amino group, hydroxyl group or carboxyl group, or substituent fused heterocyclic ring that is substituted independently by one or two or three halogen, cyano group, nitro group, amino group, hydroxyl group or carboxyl group; wherein said heterocyclic ring is imidazole, pyridine, furan, thiophene, thiazole, pyrimidine, piperazine or piperidine; said fused heterocyclic ring is quinoline or indole; and X2 is —(CH$_2$)n-, wherein n=1, 2, 3, or X2 is —O—(CH$_2$)n-, wherein n=0, 1, 2, 3.

6. The method according to claim 5, wherein the tumor is hematological tumor or malignant solid tumor.

7. The method according to claim 5, wherein: the salt is hydrochloride, phosphate, sulfate, carbonate, nitrate, citrate, tartrate, maleate, succinate, sulfonate, p-toluenesulfonate, mesylate, benzoate or fumarate.

8. A pharmaceutical composition, including: a cytidine derivative as shown in the general formula (I) or pharmaceutically acceptable salt thereof as an active ingredient, and one or more pharmaceutical carriers or excipients,

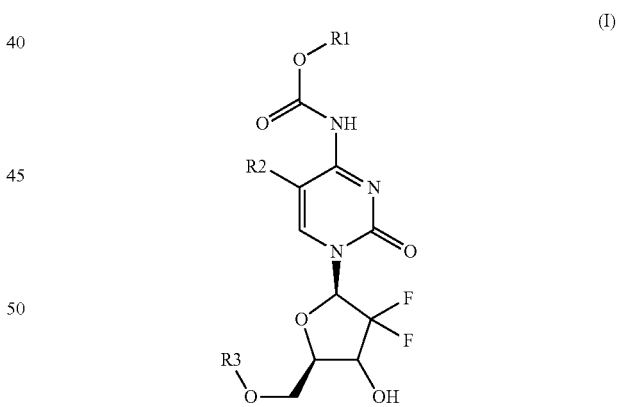

wherein, R1 is $C_1$-$C_{10}$ alkyl, $C_1$-$C_{10}$ substituent alkyl, —(CH$_2$)n-Ph, or substituent —(CH$_2$)n-Ph; wherein in said —(CH$_2$)n-Ph, n=0, 1, 2, 3 to 10, Ph is phenyl; a carbon chain of said substituent alkyl is independently substituted by one or two or three halogen, cyano group, nitro group, amino group, hydroxyl group or carboxyl group; in said substituent —(CH$_2$)n-Ph, n=0, 1, 2, 3 to 10, and a carbon chain or a phenyl ring of which is independently substituted by one or two or three halogen, cyano group, nitro group, amino group, hydroxyl group or carboxyl group;

R2 is halogen or a structure denoted as

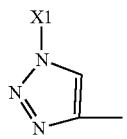

in which a line with a loose end indicating an attachment point, wherein X1 is $C_1$-$C_{10}$ alkyl, $C_1$-$C_{10}$ substituent alkyl, $C_1$-$C_{10}$ alkoxy, $C_1$-$C_{10}$ substituent alkoxy, $C_1$-$C_6$ alkylsulfonyl, $C_1$-$C_6$ alkylthiol, —(CH$_2$)n-Ph, or substituent —(CH$_2$)n-Ph; wherein a carbon chain of said substituent alkyl is substituted independently by one or two or three halogen, cyano group, nitro group, amino group, hydroxyl group or carboxyl group; a carbon chain of said substituent alkoxy is substituted independently by one or two or three halogen, cyano group, nitro group, amino group, hydroxyl group or carboxyl group; in said —(CH$_2$)n-Ph, n=0, 1, 2, 3 to 10; in said substituent —(CH$_2$)n-Ph, n=0, 1, 2, 3 to 10, and a carbon chain or a phenyl ring of which is substituted by one or two or three H, halogen, cyano group, nitro group, amino group, hydroxyl group or carboxyl group; and R3 is H or

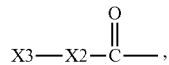

wherein X3 is phenyl ring, heterocyclic ring, fused heterocyclic ring, substituent phenyl that is substituted independently by one or two or three halogen, cyano group, nitro group, amino group, hydroxyl group or carboxyl group, substituent heterocyclic ring that is substituted independently by one or two or three halogen, cyano group, nitro group, amino group, hydroxyl group or carboxyl group, or substituent fused heterocyclic ring that is substituted independently by one or two or three halogen, cyano group, nitro group, amino group, hydroxyl group or carboxyl group; wherein said heterocyclic ring is imidazole, pyridine, furan, thiophene, thiazole, pyrimidine, piperazine or piperidine; said fused heterocyclic ring is quinoline or indole; and X2 is —(CH$_2$)n-, wherein n=1, 2, 3, or X2 is —O—(CH$_2$)n-, wherein n=0, 1, 2, 3.

9. The pharmaceutical composition according to claim 8, wherein: dosage form of the composition is injection or oral perpetration, wherein the injection refers to solution type injection, suspension type injection, emulsion type injection, or sterile powder for injection; the oral perpetration refers to tablet, powder, granule, capsule, pellet, solution, suspension, emulsion, syrup or elixir.

\* \* \* \* \*